(12) United States Patent
Nakamura et al.

(10) Patent No.: US 8,148,606 B2
(45) Date of Patent: Apr. 3, 2012

(54) PLANT BODY WITH MODIFIED PROGRAM RELATED TO ACCUMULATION OF STORAGE MATERIAL AND THE USE THEREOF

(75) Inventors: Kenzo Nakamura, Nagoya (JP); Hironaka Tsukagoshi, Nagoya (JP); Atsushi Morikami, Nagoya (JP)

(73) Assignees: National University Corporation, Nagoya-Shi (JP); Nagoya University, Nagoya-Shi (JP)

( * ) Notice: Subject to any disclaimer, the term of this patent is extended or adjusted under 35 U.S.C. 154(b) by 376 days.

(21) Appl. No.: 12/227,530

(22) PCT Filed: Oct. 10, 2006

(86) PCT No.: PCT/JP2006/320222
§ 371 (c)(1),
(2), (4) Date: Apr. 22, 2009

(87) PCT Pub. No.: WO2007/135755
PCT Pub. Date: Nov. 29, 2007

(65) Prior Publication Data
US 2011/0065941 A1 Mar. 17, 2011

(30) Foreign Application Priority Data
May 23, 2006 (JP) ................................. 2006-142455

(51) Int. Cl.
C12N 15/82 (2006.01)
C12N 15/63 (2006.01)
C12N 15/00 (2006.01)
C12N 15/10 (2006.01)
A01H 5/00 (2006.01)
A01H 5/10 (2006.01)

(52) U.S. Cl. ........ 800/285; 800/287; 800/284; 800/281; 800/295; 435/320.1; 435/468; 435/410; 536/23.1; 536/23.6; 536/24.5

(58) Field of Classification Search .................. None
See application file for complete search history.

(56) References Cited

U.S. PATENT DOCUMENTS
7,446,241 B2 * 11/2008 Rock et al. ................. 800/289

OTHER PUBLICATIONS

Tsukagoshi et al 2005 Plant Physiology 138:675-685, published in Jun. 2005, provided by Applicant.*
Tsukagoshi et al., "Functional Analysis of *Arabidopsis* Transcriptional Repressor with B3 Domain-EAR Motif." *The Molecular Biology Society of Japan Koen Yoshishu.*, vol. 28, 2005, p. 646.
Tsukagoshi et al., "Analysis of a Sugar Response Mutant of *Arabidopsis* Identified a Novel B3 Domain Protein that Functions as an Active Transcriptional Repressor." *Plant Physiol.*, 2005, vol. 138, p. 675-685.
"Accession: BH811667 {gi:20390122}, Difinition: SALK_059568. *Arabidopsis thaliana* TDNA Insertion Lines *Arabidopsis thaliana* Genomic Clone SALK_059568, Genomic Survey Sequence."NCBI Sequence Revision History [online]; May 2, 2002 uploaded, NCBI, <URL:http://www.ncbi.nlm.nih.gov/entrez/viewer.fcgi?20390122:GSS:3570541> [retrieved on Nov. 8, 2006], Retrieved from the Internet ,URL:http://www.ncbi.nlm.niih.gov/entrez/sutils/girevhist.cgi?val=BH811667++>.
Masaki T., et al. "ACTIVATOR of Spo$^{min}$ :: LUC1/WRINKLED1 of *Arabidopsis thaliana* Transactivated Sugar-inducible Promotors."*Plant Cell Physiol.*, 2005, vol. 46, No. 4, p. 547-556.
Mitsui et al., "Functional Analysis of an AP2 Factor, ASML1/WR11, Involved in Sugar-inducible Gene Expression and Control of an Oil Storage in *Arabidopsis thaliana*." *The Molecular Biology Society of Japan Koen Yoshishu.*, vol. 28, 2005, p. 420.

* cited by examiner

*Primary Examiner* — Brent T Page
(74) *Attorney, Agent, or Firm* — Oliff & Berridge, PLC

(57) ABSTRACT

The object of the invention is to provide a plant body in which the program for accumulating storage products has been modified, and applications of the same. In the invention, the plant body is constructed so as to have a B3 DNA-binding domain and an EAR motif, and so as to be capable of repressing the expression of two or more genes which code for two or more proteins having a sugar-inducible promotor function-suppressing activity.

20 Claims, 12 Drawing Sheets

Fig.1

(days)

| GeneName | Description | sGsL | KK-1 | ratio1 | Col-0 | KK-2 | ratio2 | ratio ave |
|---|---|---|---|---|---|---|---|---|
| At3g27660 | oleosin identical to oleosin isoform | 254 | 44910 | 177 | 468 | 84811 | 181 | 179 |
| At5g44120 | 12S seed storage protein (CRA1) | 3220 | 274491 | 85 | 2218 | 391692 | 177 | 131 |
| At3g01570 | oleosin similar to oleosin | 977 | 128973 | 132 | 1711 | 211362 | 124 | 128 |
| At1g47540 | trypsin inhibitor, putative | 1170 | 142929 | 122 | 2109 | 238828 | 113 | 118 |
| At4g28520 | 12S seed storage protein/ cruciferin | 1616 | 198414 | 123 | 3646 | 374243 | 103 | 113 |
| At4g27170 | 2S seed storage protein 4 | 1972 | 188665 | 96 | 3206 | 337301 | 105 | 100 |
| At5g54740 | 2S seed storage proteins | 133 | 12515 | 94 | 278 | 26395 | 95 | 95 |
| At3g22640 | cupin family protein | 642 | 50174 | 78 | 1136 | 96715 | 85 | 82 |
| At4g26740 | embryo-specific protein 1 (ATS1) | 261 | 22227 | 85 | 549 | 41213 | 75 | 80 |
| At4g25140 | glycine-rich protein / oleosin | 984 | 80352 | 82 | 2069 | 139424 | 67 | 75 |
| At1g03880 | 12S seed storage protein (CRB) | 652 | 45987 | 71 | 1034 | 80103 | 77 | 74 |
| At5g51210 | glycine-rich protein / oleosin | 1068 | 89991 | 84 | 2490 | 157681 | 63 | 74 |
| At2g31985 | expressed protein | 42 | 2896 | 69 | 69 | 5250 | 76 | 73 |
| At5g40420 | glycine-rich protein / oleosin | 685 | 47498 | 69 | 1143 | 84016 | 74 | 71 |
| At5g55240 | caleosin-related family protein | 207 | 14542 | 70 | 390 | 26643 | 68 | 69 |
| At4g27150 | 2S seed storage protein 2 | 444 | 31398 | 71 | 966 | 64337 | 67 | 69 |
| At1g03890 | cupin family protein | 236 | 15318 | 65 | 400 | 28771 | 72 | 68 |
| At5g47670 | leafy cotyledon 1-related (L1L)★ | 115 | 5236 | 46 | 112 | 9429 | 84 | 65 |
| At4g27140 | 2S seed storage protein 1 | 172 | 10769 | 62 | 357 | 24016 | 67 | 65 |
| At2g28490 | cupin family protein | 486 | 31803 | 65 | 972 | 56606 | 58 | 62 |
| At2g15010 | thionin | 304 | 10365 | 34 | 255 | 22016 | 86 | 60 |
| At5g27200 | acyl carrier protein / ACP | 431 | 23737 | 55 | 625 | 40923 | 65 | 60 |
| At1g48130 | peroxiredoxin (PER1) | 283 | 14999 | 53 | 538 | 34194 | 64 | 58 |
| At3g28150 | expressed protein | 45 | 1952 | 44 | 51 | 3535 | 69 | 56 |
| At4g30880 | lipid transfer protein (LTP) family protein | 555 | 26934 | 49 | 810 | 51201 | 63 | 56 |
| At5g01300 | phosphatidylethanolamine-binding family protein | 117 | 10082 | 86 | 938 | 20783 | 22 | 54 |
| At3g12203 | serine carboxypeptidase S10 family protein | 149 | 7636 | 51 | 252 | 12634 | 50 | 51 |
| At5g05290 | expansin, putative (EXP2) | 168 | 8659 | 52 | 192 | 8446 | 44 | 48 |
| At3g44460 | basic leucine zipper transcription factor (BZIP67)★ | 45 | 1952 | 43 | 68 | 3491 | 51 | 47 |
| At1g05510 | expressed protein | 163 | 5997 | 37 | 224 | 12173 | 54 | 46 |
| At3g63040 | expressed protein predicted protein, | 466 | 17358 | 37 | 621 | 32221 | 52 | 45 |
| At3g54940 | cysteine proteinase | 1148 | 52735 | 46 | 2856 | 99066 | 35 | 40 |
| At2g34700 | pollen Ole e 1 | 666 | 27747 | 42 | 1288 | 50189 | 39 | 40 |
| At1g67100 | LOB domain protein 40★ | 189 | 6698 | 36 | 329 | 14797 | 45 | 40 |
| At4g36700 | cupin family protein | 635 | 28554 | 45 | 2093 | 58755 | 28 | 37 |
| At1g48800 | terpene synthase/cyclase family protein | 82 | 2634 | 32 | 110 | 4474 | 41 | 36 |
| At2g05580 | unknown protein | 934 | 35487 | 38 | 1695 | 57477 | 34 | 36 |
| At4g39130 | dehydrin family protein contains | 335 | 6217 | 19 | 206 | 10614 | 52 | 35 |
| At2g23640 | reticulon family protein (RTNLB13) | 75 | 1251 | 17 | 93 | 4769 | 51 | 34 |
| At3g44300 | nitrilase 2 (NIT2) | 635 | 15882 | 25 | 684 | 27169 | 40 | 32 |

Fig.5

| GeneName | Description | sGsL | KK-1 | ratio1 | Col-0 | KK-2 | ratio2 | ratio ave. |
|---|---|---|---|---|---|---|---|---|
| At1g76930 | proline-rich extensin-like family protein | 28270 | 1175 | 0.04 | 39352 | 1043 | 0.03 | 0.03 |
| At5g42800 | dihydroflavonol 4-reductase (DFR) nearly identical | 6634 | 431 | 0.06 | 13397 | 261 | 0.02 | 0.04 |
| At1g49570 | peroxidase, putative identical to peroxidase ATP5a | 2800 | 113 | 0.04 | 2419 | 110 | 0.05 | 0.04 |
| At4g13770 | cytochrome P450 family protein | 2510 | 131 | 0.05 | 5343 | 203 | 0.04 | 0.05 |
| At3g27690 | chlorophyll A-B binding protein (LHCB2:4) | 4274 | 227 | 0.05 | 4812 | 194 | 0.04 | 0.05 |
| At1g29910 | chlorophyll A-B binding protein 2 (CAB2A) | 130417 | 7926 | 0.06 | 122887 | 4460 | 0.04 | 0.05 |
| At5g04950 | nicotianamine synthase, putative | 3677 | 248 | 0.07 | 3509 | 106 | 0.03 | 0.05 |
| At3g23430 | phosphate transporter, putative (PHO1) | 1375 | 99 | 0.07 | 2623 | 86 | 0.03 | 0.05 |
| At1g66200 | glutamine synthetase, putative | 9886 | 615 | 0.06 | 17512 | 779 | 0.04 | 0.05 |
| At1g29920 | chlorophyll A-B binding protein (LHCP) | 436448 | 24585 | 0.06 | 364051 | 19047 | 0.05 | 0.05 |
| At2g36120 | unknown protein | 13195 | 888 | 0.07 | 23172 | 996 | 0.04 | 0.06 |
| At2g34430 | chlorophyll A-B binding protein / LHCII type I (LHB1B1) | 104861 | 5707 | 0.05 | 92060 | 5210 | 0.06 | 0.06 |
| At1g24020 | Bet v I allergen family protein similar | 44669 | 4344 | 0.10 | 60032 | 982 | 0.02 | 0.06 |
| At5g23010 | 2-isopropylmalate synthase 3 (IMS3) | 1227 | 115 | 0.09 | 3106 | 69 | 0.02 | 0.06 |
| At2g37130 | peroxidase 21 (PER21) (P21) (PRXR5) | 2792 | 175 | 0.06 | 2907 | 155 | 0.05 | 0.06 |
| At3g58990 | aconitase C-terminal domain-containing protein | 1697 | 134 | 0.08 | 3296 | 125 | 0.04 | 0.06 |
| At5g14200 | 3-isopropylmalate dehydrogenase, chloroplast, | 11889 | 950 | 0.08 | 25329 | 1070 | 0.04 | 0.06 |
| At4g16260 | glycosyl hydrolase family 17 protein | 2845 | 179 | 0.06 | 4861 | 302 | 0.06 | 0.06 |
| At5g38430 | RuBisCO small subunit 1B (RBCS-1B) (ATS1B) * | 100178 | 9223 | 0.09 | 144005 | 4986 | 0.03 | 0.06 |
| At3g19710 | branched-chain amino acid aminotransferase, putative | 1410 | 138 | 0.10 | 3687 | 106 | 0.03 | 0.06 |
| At2g38380 | peroxidase 22 (PER22) (P22) (PRXEA) | 2610 | 213 | 0.08 | 4396 | 204 | 0.05 | 0.06 |
| At2g39730 | ribulose bisphosphate carboxylase/ RuBisCO activase | 63455 | 5848 | 0.09 | 81297 | 3222 | 0.04 | 0.07 |

* : ribulose bisphosphate carboxylase small chain 1B / RuBisCO small subunit 1B (RBCS-1B) (ATS1B)

Fig.6

A
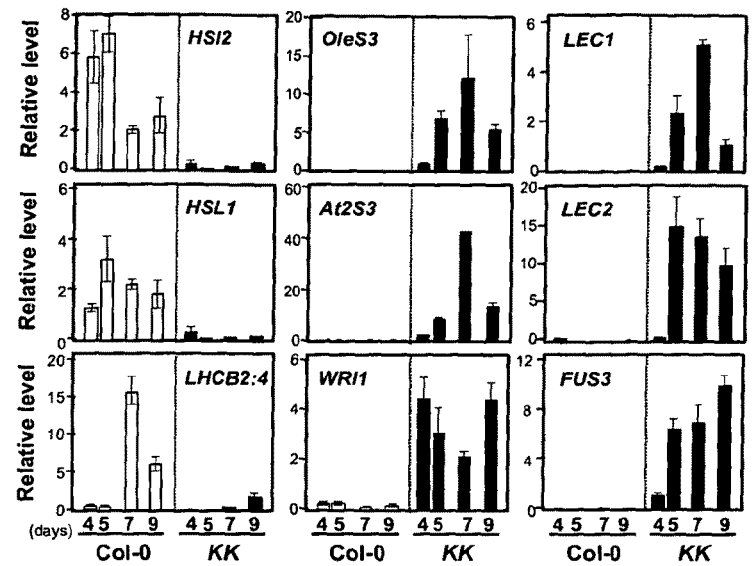
B
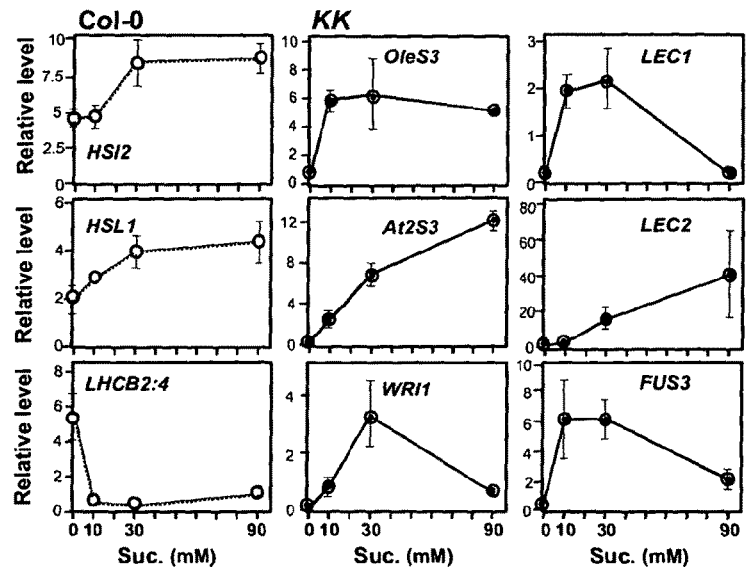
Fig. 7

A
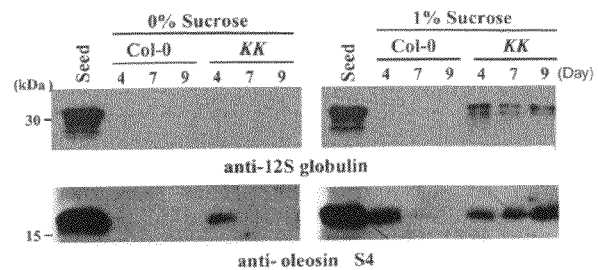
B
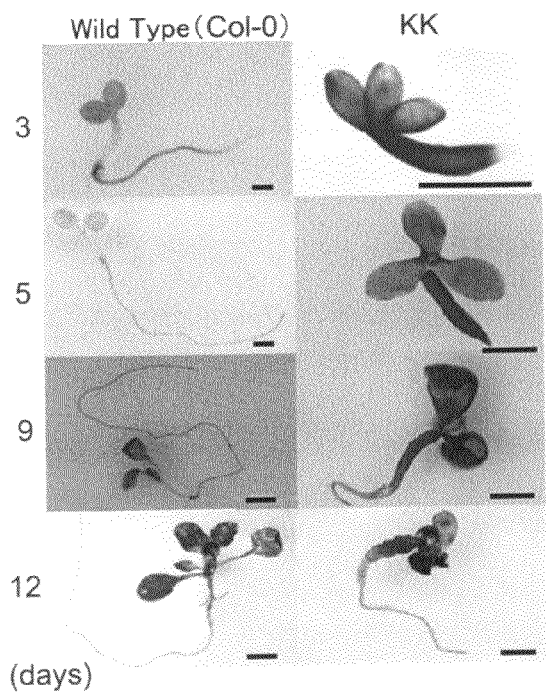
C
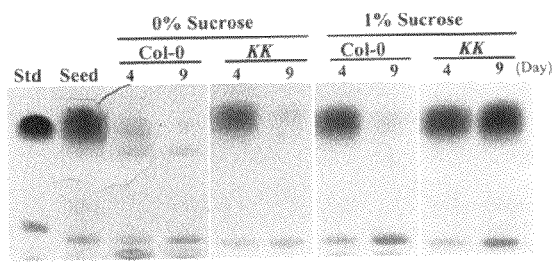
Fig.8

U S 8,148,606 B2

SEQUENCE LISTING

```
<160> NUMBER OF SEQ ID NOS: 30

<210> SEQ ID NO 1
<211> LENGTH: 2373
<212> TYPE: DNA
<213> ORGANISM: Arabidopsis thaliana

<400> SEQUENCE: 1
```

-continued

```
atgtttgaag tcaaaatggg gtcaaagatg tgcatgaacg cttcatgtgg tacgacttct      60
actgttgaat ggaagaaagg ttggcctctt cgatctggtc ttctcgctga tctctgttat     120
cgttgcggat ctgcgtatga gagttctcta ttctgtgaac aatttcataa ggaccaatct     180
ggttggaggg aatgctattt gtgtagcaag agactacatt gtggatgcat tgcttctaag     240
gtaacgattg agttaatgga ctatggtggt gttggttgta gtacatgtgc ttgctgccat     300
caactcaatt tgaacacaag gggtgagaat ccaggtgttt ttagcagatt gccaatgaaa     360
acgttagctg ataggcaaca tgtaaatggc gaaagcggag gaagaaacga aggcgatctc     420
ttttctcagc cactagtcat gggcggagat aaaagggaag agttcatgcc tcaccgtggg     480
tttggtaagc taatgagtcc agaaagtaca accaccgggc ataggctgga tgctgctggg     540
gaaatgcatg aatcatcacc tttacagcca tcttttaaata tgggtttggc tgtgaatccg     600
tttagcccat cttttgcaac cgaggctgtc gagggaatga acacatcag tccttctcag     660
tccaacatgg tccattgctc tgcttctaat atactgcaaa agccatcaag acctgctatt     720
tcaactcctc ctgtggctag taaatccgct caggcgcgga ttggaaggcc tcctgtcgaa     780
gggcgaggga gaggccactt gcttccgcgg tattggccaa aatatacgga taaagaggtt     840
cagcagatct ctggaaattt gaatttgaac attgtacctc tctttgagaa aactcttagt     900
gccagtgatg ctggtcgcat tggtcgtcta gttcttccaa aagcctgtgc agaggcatat     960
tttcctccga ttagtcaatc cgaaggcatt cctttgaaaa tccaagatgt gaggggtagg    1020
gagtggacgt tccagttcag atattggccc aataacaata gtagaatgta tgttttagaa    1080
ggtgtcactc catgcataca gtccatgatg ctacaggctg gtgatacagt aactttcagt    1140
cgggttgatc ctggcggaaa actaatcatg ggttccagga aggcagctaa tgctggagac    1200
atgcagggtt gtgggctcac caacggaaca tcaactgagg acacatcatc gtctggtgta    1260
acagaaaacc caccctccat aaatggttcc tcgtgtattt cactaatacc gaaagagttg    1320
aatggtatgc ctgagaattt gaacagtgag actaacgggg gcaggatagg tgatgatcct    1380
acacgagtta agagaagaa gagaactcga accattggtg caaaaaataa gagacttctt    1440
ttgcatagtg aagaatctat ggagctgaga ctcacttggg aagaagctca ggacttgctt    1500
cgtccctctc ctagtgtaaa gcctaccatc gttgtcattg aggagcaaga aattgaagaa    1560
tatgacgaac ctcctgtctt tggaaagagg actatagtca ctacaaaacc ttcaggtgaa    1620
caggaacgat gggcaacttg cgacgactgc tctaaatgga gaaggttacc tgtagatgct    1680
cttctttcct ttaaatggac atgtatagac aatgtttggg atgtgagtag gtgttcatgt    1740
tctgcaccgg aggagagtct gaaggaactt gagaatgttc ttaaagtagg aagagagcac    1800
aagaagagaa gaactgggga aagccaggca gcaaaaagtc agcaagaacc gtgtggtttg    1860
gacgcactgg cgagtgcagc agtcttagga gacacaatag gcgagccaga ggtagcgacc    1920
acgaccagac atccaaggca cagggctgga tgctcttgca tcgtgtgcat tcagccacca    1980
agtgggaaag gtaggcacaa gcctacatgt ggctgcactg tgtgtagcac cgtgaagaga    2040
aggttcaaga cgcttatgat gaggaggaag aagaagcagt tggagcgcga tgtaacagca    2100
gcagaagata agaagaagaa ggacatggaa ctggctgagt ctgataagag taaggaggag    2160
aaggaagtga acacagcgag aatagacctg aacagtgatc catacaataa agaagatgtt    2220
gaagctgttg cggtggagaa agaagagagt cgaaaaagag caataggaca gtgttcgggc    2280
gtggtggctc aagacgccag tgatgtttta ggagttacag agttagaagg agagggtaag    2340
aatgttcgtg aagagccgag agtttcaagc tga                                 2373
```

```
<210> SEQ ID NO 2
<211> LENGTH: 790
<212> TYPE: PRT
<213> ORGANISM: Arabidopsis thaliana

<400> SEQUENCE: 2
```

| | | | | | | | | | | | | | | |
|---|---|---|---|---|---|---|---|---|---|---|---|---|---|---|
| Met | Phe | Glu | Val | Lys | Met | Gly | Ser | Lys | Met | Cys | Met | Asn | Ala | Ser | Cys |
| 1 | | | | 5 | | | | | 10 | | | | | 15 | |
| Gly | Thr | Thr | Ser | Thr | Val | Glu | Trp | Lys | Lys | Gly | Trp | Pro | Leu | Arg | Ser |
| | | | 20 | | | | | 25 | | | | | 30 | | |
| Gly | Leu | Leu | Ala | Asp | Leu | Cys | Tyr | Arg | Cys | Gly | Ser | Ala | Tyr | Glu | Ser |
| | | 35 | | | | | 40 | | | | | 45 | | | |
| Ser | Leu | Phe | Cys | Glu | Gln | Phe | His | Lys | Asp | Gln | Ser | Gly | Trp | Arg | Glu |
| | 50 | | | | | 55 | | | | | 60 | | | | |
| Cys | Tyr | Leu | Cys | Ser | Lys | Arg | Leu | His | Cys | Gly | Cys | Ile | Ala | Ser | Lys |
| 65 | | | | | 70 | | | | | 75 | | | | | 80 |
| Val | Thr | Ile | Glu | Leu | Met | Asp | Tyr | Gly | Gly | Val | Gly | Cys | Ser | Thr | Cys |
| | | | | 85 | | | | | 90 | | | | | 95 | |
| Ala | Cys | Cys | His | Gln | Leu | Asn | Leu | Asn | Thr | Arg | Gly | Glu | Asn | Pro | Gly |
| | | | 100 | | | | | 105 | | | | | 110 | | |
| Val | Phe | Ser | Arg | Leu | Pro | Met | Lys | Thr | Leu | Ala | Asp | Arg | Gln | His | Val |
| | | | 115 | | | | | 120 | | | | | 125 | | |
| Asn | Gly | Glu | Ser | Gly | Gly | Arg | Asn | Glu | Gly | Asp | Leu | Phe | Ser | Gln | Pro |
| | 130 | | | | | 135 | | | | | 140 | | | | |
| Leu | Val | Met | Gly | Gly | Asp | Lys | Arg | Glu | Gly | Phe | Met | Pro | His | Arg | Gly |
| 145 | | | | | 150 | | | | | 155 | | | | | 160 |
| Phe | Gly | Lys | Leu | Met | Ser | Pro | Glu | Ser | Thr | Thr | Thr | Gly | His | Arg | Leu |
| | | | | 165 | | | | | 170 | | | | | 175 | |
| Asp | Ala | Ala | Gly | Glu | Met | His | Glu | Ser | Ser | Pro | Leu | Gln | Pro | Ser | Leu |
| | | | 180 | | | | | 185 | | | | | 190 | | |
| Asn | Met | Gly | Leu | Ala | Val | Asn | Pro | Phe | Ser | Pro | Ser | Phe | Ala | Thr | Glu |
| | | 195 | | | | | 200 | | | | | 205 | | | |
| Ala | Val | Glu | Gly | Met | Lys | His | Ile | Ser | Pro | Ser | Gln | Ser | Asn | Met | Val |
| | 210 | | | | | 215 | | | | | 220 | | | | |
| His | Cys | Ser | Ala | Ser | Asn | Ile | Leu | Gln | Lys | Pro | Ser | Arg | Pro | Ala | Ile |
| 225 | | | | | 230 | | | | | 235 | | | | | 240 |
| Ser | Thr | Pro | Pro | Val | Ala | Ser | Lys | Ser | Ala | Gln | Ala | Arg | Ile | Gly | Arg |
| | | | | 245 | | | | | 250 | | | | | 255 | |
| Pro | Pro | Val | Glu | Gly | Arg | Gly | Arg | Gly | His | Leu | Leu | Pro | Arg | Tyr | Trp |
| | | | 260 | | | | | 265 | | | | | 270 | | |
| Pro | Lys | Tyr | Thr | Asp | Lys | Glu | Val | Gln | Gln | Ile | Ser | Gly | Asn | Leu | Asn |
| | | 275 | | | | | 280 | | | | | 285 | | | |
| Leu | Asn | Ile | Val | Pro | Leu | Phe | Glu | Lys | Thr | Leu | Ser | Ala | Ser | Asp | Ala |
| | 290 | | | | | 295 | | | | | 300 | | | | |
| Gly | Arg | Ile | Gly | Arg | Leu | Val | Leu | Pro | Lys | Ala | Cys | Ala | Glu | Ala | Tyr |
| 305 | | | | | 310 | | | | | 315 | | | | | 320 |
| Phe | Pro | Pro | Ile | Ser | Gln | Ser | Glu | Gly | Ile | Pro | Leu | Lys | Ile | Gln | Asp |
| | | | | 325 | | | | | 330 | | | | | 335 | |
| Val | Arg | Gly | Arg | Glu | Trp | Thr | Phe | Gln | Phe | Arg | Tyr | Trp | Pro | Asn | Asn |
| | | | 340 | | | | | 345 | | | | | 350 | | |
| Asn | Ser | Arg | Met | Tyr | Val | Leu | Glu | Gly | Val | Thr | Pro | Cys | Ile | Gln | Ser |
| | | 355 | | | | | 360 | | | | | 365 | | | |
| Met | Met | Leu | Gln | Ala | Gly | Asp | Thr | Val | Thr | Phe | Ser | Arg | Val | Asp | Pro |
| | 370 | | | | | 375 | | | | | 380 | | | | |

```
Gly Gly Lys Leu Ile Met Gly Ser Arg Lys Ala Ala Asn Ala Gly Asp
385                 390                 395                 400
Met Gln Gly Cys Gly Leu Thr Asn Gly Thr Ser Thr Glu Asp Thr Ser
            405                 410                 415
Ser Ser Gly Val Thr Glu Asn Pro Pro Ser Ile Asn Gly Ser Ser Cys
            420                 425                 430
Ile Ser Leu Ile Pro Lys Glu Leu Asn Gly Met Pro Glu Asn Leu Asn
            435                 440                 445
Ser Glu Thr Asn Gly Gly Arg Ile Gly Asp Asp Pro Thr Arg Val Lys
            450                 455                 460
Glu Lys Lys Arg Thr Arg Thr Ile Gly Ala Lys Asn Lys Arg Leu Leu
465                 470                 475                 480
Leu His Ser Glu Glu Ser Met Glu Leu Arg Leu Thr Trp Glu Ala
            485                 490                 495
Gln Asp Leu Leu Arg Pro Ser Pro Ser Val Lys Pro Thr Ile Val Val
            500                 505                 510
Ile Glu Glu Gln Glu Ile Glu Tyr Asp Glu Pro Val Phe Gly
            515                 520                 525
Lys Arg Thr Ile Val Thr Thr Lys Pro Ser Gly Glu Gln Glu Arg Trp
            530                 535                 540
Ala Thr Cys Asp Asp Cys Ser Lys Trp Arg Arg Leu Pro Val Asp Ala
545                 550                 555                 560
Leu Leu Ser Phe Lys Trp Thr Cys Ile Asp Asn Val Trp Asp Val Ser
            565                 570                 575
Arg Cys Ser Cys Ser Ala Pro Glu Glu Ser Leu Lys Glu Leu Glu Asn
            580                 585                 590
Val Leu Lys Val Gly Arg Glu His Lys Lys Arg Arg Thr Gly Glu Ser
            595                 600                 605
Gln Ala Ala Lys Ser Gln Gln Glu Pro Cys Gly Leu Asp Ala Leu Ala
            610                 615                 620
Ser Ala Ala Val Leu Gly Asp Thr Ile Gly Glu Pro Glu Val Ala Thr
625                 630                 635                 640
Thr Thr Arg His Pro Arg His Arg Ala Gly Cys Ser Cys Ile Val Cys
            645                 650                 655
Ile Gln Pro Pro Ser Gly Lys Gly Arg His Lys Pro Thr Cys Gly Cys
            660                 665                 670
Thr Val Cys Ser Thr Val Lys Arg Arg Phe Lys Thr Leu Met Met Arg
            675                 680                 685
Arg Lys Lys Lys Gln Leu Glu Arg Asp Val Thr Ala Ala Glu Asp Lys
            690                 695                 700
Lys Lys Lys Asp Met Glu Leu Ala Glu Ser Asp Lys Ser Lys Glu Glu
705                 710                 715                 720
Lys Glu Val Asn Thr Ala Arg Ile Asp Leu Asn Ser Asp Pro Tyr Asn
            725                 730                 735
Lys Glu Asp Val Glu Ala Val Ala Val Glu Lys Glu Ser Arg Lys
            740                 745                 750
Arg Ala Ile Gly Gln Cys Ser Gly Val Val Ala Gln Asp Ala Ser Asp
            755                 760                 765
Val Leu Gly Val Thr Glu Leu Glu Gly Glu Gly Lys Asn Val Arg Glu
            770                 775                 780
Glu Pro Arg Val Ser Ser
785                 790
```

```
<210> SEQ ID NO 3
<211> LENGTH: 2343
<212> TYPE: DNA
<213> ORGANISM: Arabidopsis thaliana

<400> SEQUENCE: 3
atggagtcaa taaaggtttg catgaacgca ctgtgcggag cggcctctac gtcgggcgag      60
tggaaaaaag ctggcctat gcgatccggt gatttagctt ctctctgcga taagtgtggg      120
tgtgcatacg agcaatccat attctgtgaa gtgttccatg ccaaggaatc tggttggaga      180
gagtgtaatt catgtgacaa gcgtcttcac tgtggatgca ttgcttctag atttatgatg      240
gagcttctag agaatggtgg tgttacctgt ataagttgcg ccaagaaatc cggactaatt      300
tctatgaatg tgagccatga atctaacggt aaggacttcc cctcatttgc ttcagcagag      360
catgtaggca gtgttcttga aggacaaat ctcaagcact tgcttcactt tcaaagaatc      420
gaccccactc attcttctct tcaaatgaaa caagaagaat cgctgcttcc ttccagccta      480
gatgctctta gacacaaaac tgaaaggaaa gaattgtctg cacagccaaa cttgagcatt      540
tcacttggac ctacgcttat gacaagccca tttcatgatg ctgctgttga tgacagaagt      600
aagactaatt cgattttcca actggcccct cggtccaggc agctgcttcc aaaacctgca      660
aattcagctc ccattgctgc tggcatggag cctagtggga gcctggtgtc acagattcat      720
gtcgctcggc ctcctccaga aggtcgcggg aagacccaat gcttccccg ttactggcct      780 aggattactg accaagagct gctgcaatta tctggacagt atcctcatct ctcaaattcc      840
aaaattatac cactctttga aaagttctg agtgcgagcg atgcgggtcg tattggtcga      900
ctggttcttc cgaaagcatg tgcagaggca tatttccccc ctatatctct acccgagggt      960
ctcccgttaa agatacaaga cataaaaggg aagaatggg tgttccagtt caggttttgg      1020
cctaataata acagcaggat gtacgttttg gagggtgtga ctccttgcat acagtccatg      1080
cagttgcaag ctggtgacac tgtaacattc agccgtacag aacctgaagg aaaactcgta      1140
atgggatacc gtaaagcgac gaactctaca gcgacacaga tgttcaaggg aagcagtgaa      1200
cccaatctga acatgttttc caacagcttg aatccgggat gtggtgacat caattggtct      1260
aaactagaga agtctgagga catggcaaag gataacttat ttcttcagtc gtccttaact      1320
tctgctagga acgggttcg gaacattggg actaagagca agcgtctgct cattgatagc      1380
gtagatgttc tggaactgaa aataacttgg gaggaggcac aggagctgtt gcggcctccc      1440
caatccacca aacccagcat ctttacgctg aaaatcaag attttgaaga atatgacgaa      1500
ccaccagttt tcgggaagag gaccctttt gtctcacgtc aaacagggga acaagagcaa      1560
tgggtgcagt gtgatgcttg tgggaaatgg cgacagctgc cggtggatat tcttcttcca      1620
ccaaagtggt cgtgctctga taatctcttg gatcctggca ggtcttcatg ttccgcacct      1680
gatgaactct ctccaagaga acaggataca cttgtccggc agagcaaaga gttcaaaagg      1740
aggagactgg catcatcaaa cgaaaagcta accagtcgc aggatgcatc tgctctgaat      1800
agtttaggaa atgcaggcat caccacaacc ggtgaacagg gggaaatcac ggttgcagcc      1860
acgaccaagc atccaagaca ccgggcaggg tgttcgtgca tcgtctgcag ccaaccaccg      1920
agcggaaaag gcaaacacaa gccgtcatgc acttgcactg tgtgcgaggc agtgaagaga      1980
cgattcagga cgctcatgct gcggaagcgg aacaaaggag aggcaggaca ggcaagccag      2040
caggcgcagt cacagtcaga gtgcagggac gagacagaag tggagagcat tccagcggtt      2100
gaactagccg caggggaaaa catcgacttg aactcagacc cggggggcttc ccgagtaagc      2160 atgatgaggc ttctccaagc tgcagcgttt cctctggaag catatctgaa acaaaaggct      2220
```

```
atttccaata cagcaggaga acagcaaagc agtgatatgg tcagcacaga acacggttcg    2280
tcctcagccg cacaagaaac tgagaaagac acaacaaatg gagctcatga tcctgtgaac    2340
taa                                                                   2343

<210> SEQ ID NO 4
<211> LENGTH: 780
<212> TYPE: PRT
<213> ORGANISM: Arabidopsis thaliana

<400> SEQUENCE: 4

Met Glu Ser Ile Lys Val Cys Met Asn Ala Leu Cys Gly Ala Ala Ser
1               5                   10                  15

Thr Ser Gly Glu Trp Lys Lys Gly Trp Pro Met Arg Ser Gly Asp Leu
            20                  25                  30

Ala Ser Leu Cys Asp Lys Cys Gly Cys Ala Tyr Glu Gln Ser Ile Phe
        35                  40                  45

Cys Glu Val Phe His Ala Lys Glu Ser Gly Trp Arg Glu Cys Asn Ser
    50                  55                  60

Cys Asp Lys Arg Leu His Cys Gly Cys Ile Ala Ser Arg Phe Met Met
65                  70                  75                  80

Glu Leu Leu Glu Asn Gly Gly Val Thr Cys Ile Ser Cys Ala Lys Lys
                85                  90                  95

Ser Gly Leu Ile Ser Met Asn Val Ser His Glu Ser Asn Gly Lys Asp
            100                 105                 110

Phe Pro Ser Phe Ala Ser Ala Glu His Val Gly Ser Val Leu Glu Arg
        115                 120                 125

Thr Asn Leu Lys His Leu Leu His Phe Gln Arg Ile Asp Pro Thr His
    130                 135                 140

Ser Ser Leu Gln Met Lys Gln Glu Glu Ser Leu Leu Pro Ser Ser Leu
145                 150                 155                 160

Asp Ala Leu Arg His Lys Thr Glu Arg Lys Glu Leu Ser Ala Gln Pro
                165                 170                 175

Asn Leu Ser Ile Ser Leu Gly Pro Thr Leu Met Thr Ser Pro Phe His
            180                 185                 190

Asp Ala Ala Val Asp Asp Arg Ser Lys Thr Asn Ser Ile Phe Gln Leu
        195                 200                 205

Ala Pro Arg Ser Arg Gln Leu Leu Pro Lys Pro Ala Asn Ser Ala Pro
    210                 215                 220

Ile Ala Ala Gly Met Glu Pro Ser Gly Ser Leu Val Ser Gln Ile His
225                 230                 235                 240

Val Ala Arg Pro Pro Glu Gly Arg Gly Lys Thr Gln Leu Leu Pro
                245                 250                 255

Arg Tyr Trp Pro Arg Ile Thr Asp Gln Glu Leu Leu Gln Leu Ser Gly
            260                 265                 270

Gln Tyr Pro His Leu Ser Asn Ser Lys Ile Ile Pro Leu Phe Glu Lys
        275                 280                 285

Val Leu Ser Ala Ser Asp Ala Gly Arg Ile Gly Arg Leu Val Leu Pro
    290                 295                 300

Lys Ala Cys Ala Glu Ala Tyr Phe Pro Pro Ile Ser Leu Pro Glu Gly
305                 310                 315                 320

Leu Pro Leu Lys Ile Gln Asp Ile Lys Gly Lys Glu Trp Val Phe Gln
                325                 330                 335

Phe Arg Phe Trp Pro Asn Asn Asn Ser Arg Met Tyr Val Leu Glu Gly
            340                 345                 350
```

```
Val Thr Pro Cys Ile Gln Ser Met Gln Leu Gln Ala Gly Asp Thr Val
            355                 360                 365
Thr Phe Ser Arg Thr Glu Pro Glu Gly Lys Leu Val Met Gly Tyr Arg
    370                 375                 380
Lys Ala Thr Asn Ser Thr Ala Thr Gln Met Phe Lys Gly Ser Ser Glu
385                 390                 395                 400
Pro Asn Leu Asn Met Phe Ser Asn Ser Leu Asn Pro Gly Cys Gly Asp
                405                 410                 415
Ile Asn Trp Ser Lys Leu Glu Lys Ser Glu Asp Met Ala Lys Asp Asn
            420                 425                 430
Leu Phe Leu Gln Ser Ser Leu Thr Ser Ala Arg Lys Arg Val Arg Asn
        435                 440                 445
Ile Gly Thr Lys Ser Lys Arg Leu Leu Ile Asp Ser Val Asp Val Leu
    450                 455                 460
Glu Leu Lys Ile Thr Trp Glu Glu Ala Gln Glu Leu Leu Arg Pro Pro
465                 470                 475                 480
Gln Ser Thr Lys Pro Ser Ile Phe Thr Leu Glu Asn Gln Asp Phe Glu
                485                 490                 495
Glu Tyr Asp Glu Pro Pro Val Phe Gly Lys Arg Thr Leu Phe Val Ser
            500                 505                 510
Arg Gln Thr Gly Glu Gln Glu Gln Trp Val Gln Cys Asp Ala Cys Gly
        515                 520                 525
Lys Trp Arg Gln Leu Pro Val Asp Ile Leu Leu Pro Pro Lys Trp Ser
    530                 535                 540
Cys Ser Asp Asn Leu Leu Asp Pro Gly Arg Ser Ser Cys Ser Ala Pro
545                 550                 555                 560
Asp Glu Leu Ser Pro Arg Glu Gln Asp Thr Leu Val Arg Gln Ser Lys
                565                 570                 575
Glu Phe Lys Arg Arg Arg Leu Ala Ser Ser Asn Glu Lys Leu Asn Gln
            580                 585                 590
Ser Gln Asp Ala Ser Ala Leu Asn Ser Leu Gly Asn Ala Gly Ile Thr
        595                 600                 605
Thr Thr Gly Glu Gln Gly Glu Ile Thr Val Ala Ala Thr Thr Lys His
    610                 615                 620
Pro Arg His Arg Ala Gly Cys Ser Cys Ile Val Cys Ser Gln Pro Pro
625                 630                 635                 640
Ser Gly Lys Gly Lys His Lys Pro Ser Cys Thr Cys Thr Val Cys Glu
                645                 650                 655
Ala Val Lys Arg Arg Phe Arg Thr Leu Met Leu Arg Lys Arg Asn Lys
            660                 665                 670
Gly Glu Ala Gly Gln Ala Ser Gln Gln Ala Gln Ser Gln Ser Glu Cys
        675                 680                 685
Arg Asp Glu Thr Glu Val Glu Ser Ile Pro Ala Val Glu Leu Ala Ala
    690                 695                 700
Gly Glu Asn Ile Asp Leu Asn Ser Asp Pro Gly Ala Ser Arg Val Ser
705                 710                 715                 720
Met Met Arg Leu Leu Gln Ala Ala Ala Phe Pro Leu Glu Ala Tyr Leu
                725                 730                 735
Lys Gln Lys Ala Ile Ser Asn Thr Ala Gly Glu Gln Gln Ser Ser Asp
            740                 745                 750
Met Val Ser Thr Glu His Gly Ser Ser Ala Ala Gln Glu Thr Glu
        755                 760                 765
Lys Asp Thr Thr Asn Gly Ala His Asp Pro Val Asn
```

```
                     770            775             780
```

<210> SEQ ID NO 5
<211> LENGTH: 289
<212> TYPE: DNA
<213> ORGANISM: Sweet potato

<400> SEQUENCE: 5
aagctttagt aaaagcattg gacacttgga cggccacaaa tcatttctat tatttctccc    60 aaatcattc tgttatcaac tttatctcat cccatatcta gacaccgtaa gtgttccatc    120
catcggtcta gagcaaaata atcttaaaat tgtacaaaaa acaataattc aaccttatct   180
cttgttgtct ataaattgga tgcatgcatg agagcccaac acaacacacc aacaaattaa   240
acatcattac ctcttagctt tctcccaagt tgtcatctca tctgccacc                289

<210> SEQ ID NO 6
<211> LENGTH: 108
<212> TYPE: PRT
<213> ORGANISM: Arabidopsis thaliana

<400> SEQUENCE: 6

Leu Phe Glu Lys Ala Val Thr Pro Ser Asp Val Gly Lys Leu Asn Arg
1               5                   10                  15

Leu Val Ile Pro Lys His His Ala Glu Lys His Phe Pro Leu Pro Ser
            20                  25                  30

Ser Asn Val Ser Val Lys Gly Val Leu Leu Asn Phe Glu Asp Val Asn
        35                  40                  45

Gly Lys Val Trp Arg Phe Arg Tyr Ser Tyr Trp Asn Ser Ser Gln Ser
    50                  55                  60

Tyr Val Leu Thr Lys Gly Trp Ser Arg Phe Val Lys Glu Lys Asn Leu
65                  70                  75                  80

Arg Ala Gly Asp Val Val Ser Phe Ser Arg Ser Asn Gly Gln Asp Gln
                85                  90                  95

Gln Leu Tyr Ile Gly Trp Lys Ser Arg Ser Gly Ser
            100                 105

<210> SEQ ID NO 7
<211> LENGTH: 27
<212> TYPE: DNA
<213> ORGANISM: Artificial Sequence
<220> FEATURE:
<223> OTHER INFORMATION: Synthetic Construct synthetic primer

<400> SEQUENCE: 7
gtatcaccag cctgtagcat catggac                                          27

<210> SEQ ID NO 8
<211> LENGTH: 26
<212> TYPE: DNA
<213> ORGANISM: Artificial Sequence
<220> FEATURE:
<223> OTHER INFORMATION: Synthetic Construct synthetic primer

<400> SEQUENCE: 8
aggcagctaa tgctggagac atgcag                                           26

<210> SEQ ID NO 9
<211> LENGTH: 23
<212> TYPE: DNA
<213> ORGANISM: Artificial Sequence
<220> FEATURE:
<223> OTHER INFORMATION: Synthetic Construct synthetic primer

```
<400> SEQUENCE: 9
tttcgcctgc tggggcaaac cag                                           23

<210> SEQ ID NO 10
<211> LENGTH: 24
<212> TYPE: DNA
<213> ORGANISM: Artificial Sequence
<220> FEATURE:
<223> OTHER INFORMATION: Synthetic Construct synthetic primer

<400> SEQUENCE: 10
aagcatcaca ctgcacccat tgct                                          24

<210> SEQ ID NO 11
<211> LENGTH: 25
<212> TYPE: DNA
<213> ORGANISM: Artificial Sequence
<220> FEATURE:
<223> OTHER INFORMATION: Synthetic Construct synthetic primer

<400> SEQUENCE: 11
tcggaacatt gggactaaga gcaag                                         25

<210> SEQ ID NO 12
<211> LENGTH: 25
<212> TYPE: DNA
<213> ORGANISM: Artificial Sequence
<220> FEATURE:
<223> OTHER INFORMATION: Synthetic Construct synthetic primer

<400> SEQUENCE: 12
ctgttgacta cgagcaggag atgga                                         25

<210> SEQ ID NO 13
<211> LENGTH: 25
<212> TYPE: DNA
<213> ORGANISM: Artificial Sequence
<220> FEATURE:
<223> OTHER INFORMATION: Synthetic Construct synthetic primer

<400> SEQUENCE: 13
gacttctggg catctgaatc tctca                                         25

<210> SEQ ID NO 14
<211> LENGTH: 24
<212> TYPE: DNA
<213> ORGANISM: Artificial Sequence
<220> FEATURE:
<223> OTHER INFORMATION: Synthetic Construct synthetic primer

<400> SEQUENCE: 14
cttccatatc agcttgaaac tctc                                          24

<210> SEQ ID NO 15
<211> LENGTH: 24
<212> TYPE: DNA
<213> ORGANISM: Artificial Sequence
<220> FEATURE:
<223> OTHER INFORMATION: Synthetic Construct synthetic primer

<400> SEQUENCE: 15
tggctcaaga cgccagtgat gttt                                          24

<210> SEQ ID NO 16
<211> LENGTH: 25
```

```
<212> TYPE: DNA
<213> ORGANISM: Artificial Sequence
<220> FEATURE:
<223> OTHER INFORMATION: Synthetic Construct synthetic primer

<400> SEQUENCE: 16
atgaggcttc tccaagctgc agcgt                                   25

<210> SEQ ID NO 17
<211> LENGTH: 25
<212> TYPE: DNA
<213> ORGANISM: Artificial Sequence
<220> FEATURE:
<223> OTHER INFORMATION: Synthetic Construct synthetic primer

<400> SEQUENCE: 17
gaaccgtgtt ctgtgctgac catat                                   25

<210> SEQ ID NO 18
<211> LENGTH: 24
<212> TYPE: DNA
<213> ORGANISM: Artificial Sequence
<220> FEATURE:
<223> OTHER INFORMATION: Synthetic Construct synthetic primer

<400> SEQUENCE: 18
gtaaaggtcc gatcgaaaat ctgt                                    24

<210> SEQ ID NO 19
<211> LENGTH: 25
<212> TYPE: DNA
<213> ORGANISM: Artificial Sequence
<220> FEATURE:
<223> OTHER INFORMATION: Synthetic Construct synthetic primer

<400> SEQUENCE: 19
ttatccgatc aaactctatt ttccg                                   25

<210> SEQ ID NO 20
<211> LENGTH: 23
<212> TYPE: DNA
<213> ORGANISM: Artificial Sequence
<220> FEATURE:
<223> OTHER INFORMATION: Synthetic Construct synthetic primer

<400> SEQUENCE: 20
aggcagattg ctaaagctgc aac                                     23

<210> SEQ ID NO 21
<211> LENGTH: 18
<212> TYPE: DNA
<213> ORGANISM: Artificial Sequence
<220> FEATURE:
<223> OTHER INFORMATION: Synthetic Construct synthetic primer

<400> SEQUENCE: 21
actgtgatga gagccggg                                           18

<210> SEQ ID NO 22
<211> LENGTH: 24
<212> TYPE: DNA
<213> ORGANISM: Artificial Sequence
<220> FEATURE:
<223> OTHER INFORMATION: Synthetic Construct synthetic primer

<400> SEQUENCE: 22
agcaaaacat ggctaacaag ctct                                    24
```

<210> SEQ ID NO 23
<211> LENGTH: 22
<212> TYPE: DNA
<213> ORGANISM: Artificial Sequence
<220> FEATURE:
<223> OTHER INFORMATION: Synthetic Construct synthetic primer

<400> SEQUENCE: 23
ctggcatctc tgtcttggac ct                                    22

<210> SEQ ID NO 24
<211> LENGTH: 21
<212> TYPE: DNA
<213> ORGANISM: Artificial Sequence
<220> FEATURE:
<223> OTHER INFORMATION: Synthetic Construct synthetic primer

<400> SEQUENCE: 24
accagctcag tcgtagtagc c                                     21

<210> SEQ ID NO 25
<211> LENGTH: 27
<212> TYPE: DNA
<213> ORGANISM: Artificial Sequence
<220> FEATURE:
<223> OTHER INFORMATION: Synthetic Construct synthetic primer

<400> SEQUENCE: 25
gtgagacggt aaggttttac gcatgat                               27

<210> SEQ ID NO 26
<211> LENGTH: 20
<212> TYPE: DNA
<213> ORGANISM: Artificial Sequence
<220> FEATURE:
<223> OTHER INFORMATION: Synthetic Construct synthetic primer

<400> SEQUENCE: 26
ctctctctct ctccgggaaa                                       20

<210> SEQ ID NO 27
<211> LENGTH: 20
<212> TYPE: DNA
<213> ORGANISM: Artificial Sequence
<220> FEATURE:
<223> OTHER INFORMATION: Synthetic Construct synthetic primer

<400> SEQUENCE: 27
ccatctgctc caccgggtat                                       20

<210> SEQ ID NO 28
<211> LENGTH: 30
<212> TYPE: DNA
<213> ORGANISM: Artificial Sequence
<220> FEATURE:
<223> OTHER INFORMATION: Synthetic Construct synthetic primer

<400> SEQUENCE: 28
tctttgggac aaaagctctt ggaattcgat                            30

<210> SEQ ID NO 29
<211> LENGTH: 26
<212> TYPE: DNA
<213> ORGANISM: Artificial Sequence
<220> FEATURE:
<223> OTHER INFORMATION: Synthetic Construct synthetic primer -continued

```
<400> SEQUENCE: 29 tacgtatgtgctgctgcttcttcact                                              26

<210> SEQ ID NO 30
<211> LENGTH: 111
<212> TYPE: PRT
<213> ORGANISM: Zea maize

<400> SEQUENCE: 30
```

| Asn | Leu | Arg | Phe | Leu | Leu | Gln | Lys | Val | Leu | Lys | Gln | Ser | Asp | Val | Gly |
|---|---|---|---|---|---|---|---|---|---|---|---|---|---|---|---|
| 1 | | | | 5 | | | | | 10 | | | | | 15 | |

| Ser | Leu | Gly | Arg | Ile | Val | Leu | Pro | Lys | Lys | Glu | Ala | Glu | Val | His | Leu |
|---|---|---|---|---|---|---|---|---|---|---|---|---|---|---|---|
| | | | 20 | | | | | 25 | | | | | 30 | | |

| Pro | Glu | Leu | Lys | Thr | Arg | Asp | Gly | Ile | Ser | Ile | Pro | Met | Glu | Asp | Ile |
|---|---|---|---|---|---|---|---|---|---|---|---|---|---|---|---|
| | | | 35 | | | | 40 | | | | | 45 | | | |

| Gly | Thr | Ser | Arg | Val | Trp | Asn | Met | Arg | Tyr | Arg | Phe | Trp | Pro | Asn | Asn |
|---|---|---|---|---|---|---|---|---|---|---|---|---|---|---|---|
| | 50 | | | | | 55 | | | | | 60 | | | | |

| Lys | Ser | Arg | Met | Tyr | Leu | Leu | Glu | Asn | Thr | Gly | Glu | Phe | Val | Arg | Ser |
|---|---|---|---|---|---|---|---|---|---|---|---|---|---|---|---|
| 65 | | | | | 70 | | | | | 75 | | | | | 80 |

| Asn | Glu | Leu | Gln | Glu | Gly | Asp | Phe | Ile | Val | Ile | Tyr | Ser | Asp | Val | Lys |
|---|---|---|---|---|---|---|---|---|---|---|---|---|---|---|---|
| | | | | 85 | | | | | 90 | | | | | 95 | |

| Ser | Gly | Lys | Tyr | Leu | Ile | Arg | Gly | Val | Lys | Val | Arg | Pro | Pro | Pro | |
|---|---|---|---|---|---|---|---|---|---|---|---|---|---|---|---|
| | | | 100 | | | | | 105 | | | | | 110 | | |

PLANT BODY WITH MODIFIED PROGRAM RELATED TO ACCUMULATION OF STORAGE MATERIAL AND THE USE THEREOF

TECHNICAL FIELD

The present invention relates to technology of modifying the operability of programs relating to the accumulation of storage products and embryogenesis in plants.

BACKGROUND ART

Plants accumulate storage products in seeds, tubers and tuberous roots. Commonly known storage products include storage proteins, storage starches and storage oils. These storage products, along with serving as sources of nutrition for young plants until they become capable of autotrophic growth by means of photosynthesis, are also an important source of nutrition for animals—including man, and also serve as industrial starting materials. Such storage products generally are accumulated only at specific periods and in specific tissue associated with maturation of the plant. However, were one to have the ability to control the storage product accumulating functions of a plant, it may then be possible to modify the accumulation of storage products in terms of period, place, or quantitatively and qualitatively, and thus obtain such storage products at will. Various investigations are being conducted on the accumulation of storage products in plants towards this very end.

For example, three proteins, ABI3, FUS3 and LEC2 having the plant-specific B3 DNA-binding domain, are known to be transcriptional control factors which regulate the maturation program that includes the accumulation of storage proteins and oils in the seeds of mouse-ear cress (*Arabidopsis thaliana*). These proteins have been reported to regulate the seed maturation program together with the transcription factor LEC1 and the plant hormone abscisic acid (*Int J Dev Biol* 56, 645-651 (2005)). Elsewhere, the inventors have identified HSI2, HSI2-L1 (also referred to below as "HSL1") and HSI2-L2 (also referred to below as "HSL2"), which are similarly B3 DNA domain-binding proteins, as transcriptional control factors associated with sugar responsive gene expression control, and conducted analyses on these factors (*Plant Physiol* 138, 675-685 (2005); *Plant Biotech* 22, 371-377 (2005)). It is known that these transcriptional control factors all have the B3 DNA-binding domain, and that a sequence similar to the transcriptional repression motif EAR is present on the C-terminal side thereof.

In addition, an attempt to increase the oil content of seeds by genetic manipulation (Japanese Patent Application Laid-open No. H9-313059) and the accumulation of oils in root tips as a result of mutations (*Science* 277, 91-94 (1997)) have been disclosed.

DISCLOSURE OF THE INVENTION

HSI2, HSI2-L1 and HSI2-L2 make up a different subfamily of transcriptional control factors than the above-mentioned proteins ABI3, FUS3 and LEC2, however, the functions of the transcriptional control factors belonging to the HSI2 subfamily are not yet clear. Moreover, the genetic control mechanisms thereof involved in the accumulation of storage products such as storage oils in plants is not yet well understood.

It is an object of the present invention may be to provide a plant body in which the program for accumulating storage products is modified, and applications thereof. Another object of the invention may be to provide a plant body capable of accumulating storage products in organs other than the normal storage organs or in periods other than the normal storage product accumulation periods, and applications thereof. Yet another object of the invention may be to provide a method of producing plant storage products.

The inventors have discovered that when the seeds of a plant homodeficient for two transcription factors associated with sugar-inducible gene expression regulation, which is obtained by crossing plants which are each homodeficient for respective transcription factors as aforestated, are germinated in the presence of sugar, the seedlings reproduce an embryogenic state without exhibiting the normal seedling growth, and storage products such as oils accumulate in the hypocotyls. In addition, the inventors have also found that, following the germination of the seeds of this homodeficient plant, the expression level of various storage-related genes increases while on the other hand the expression level of photosynthesis-related genes decreases, and that the hypocotyl following germination manifests an embryogenic state similar to that of the seed. The following inventions are provided based on these discoveries.

This invention provides a plant body being constructed so as to be capable of repressing expression of two or more genes coding for two or more proteins, each of the proteins comprises a B3 DNA-binding domain and an EAR motif and has a suppressing activity to suppress function of a sugar-inducible promoter. In the present invention, it is preferable that the sugar-inducible promoter is a sugar-inducible sweet potato sporamin minimal promoter.

In the present invention, the two or more proteins may be one or two or more of first proteins selected from among (a1) to (a3) below and one or two or more of second proteins selected from among (b1) to (b3) below. The plant body of the present invention may possess an extrinsic factor capable of repressing the expression of genes respectively coding for the first protein and the second protein.

(a1) a protein which comprises an amino acid sequence of SEQ ID NO: 2;

(a2) a protein which comprises an amino acid sequence having one or more amino acids substituted, deleted, inserted and/or added in the amino acid sequence of SEQ ID NO: 2, and has an activity of the same nature as a protein with the amino acid sequence of SEQ ID NO: 2;

(a3) a protein which hybridizes under stringent conditions to DNA having a base sequence of SEQ ID NO: 1 or to a part of a complementary strand thereto, and has the activity of the same nature as the protein with the amino acid sequence of SEQ ID NO: 2;

(b1) a protein which comprises an amino acid sequence of SEQ ID NO: 4;

(b2) a protein which comprises an amino acid sequence having one or more amino acids substituted, deleted, inserted and/or added in the amino acid sequence of SEQ ID NO: 4, and has an activity of the same nature as the protein with the amino acid sequence of SEQ ID NO: 4;

(b3) a protein which hybridizes under stringent conditions to DNA having a base sequence of SEQ ID NO: 3 or to a part of a complementary strand thereto, and has the activity of the same nature as the protein with the amino acid sequence of SEQ ID NO: 4.

The plant body of present invention may exhibit sugar-induced late embryogenesis-type gene expression or exhibit gene expression in which the expression level increases for one or two or more genes selected from among genes coding for sugar-induced storage product-related proteins and transcription factor genes that positively regulate the genes coding for storage product-related proteins, and in which the expression level decreases for one or two or more genes selected from among photosynthesis-related genes. Further, the plant body of the present invention may produce a storage product by sugar induction. The storage product may be a storage product in seed and preferably it may contain oil.

The plant body of the present invention may be part or all of a plant individual. In this case, the plant body may accumulate a storage product at a site other than the normal storage organ by sugar induction or the plant individual may be a seedling individual which accumulates the storage product in a hypocotyl. Further, the plant body of the present invention, the plant may be a seed, preferably the seed may accumulate a storage product by sugar induction in a hypocotyl of a seedling individual that is germinated. The plant body of the present invention, the plant may be a cultured tissue. In this aspect, the cultured may be a callus. The plant body of the present invention, the plant body may be a plant cell.

The plant body of the present invention, the plant body may be mouse-ear cress (*Arabidopsis thaliana*) or derived from said plant species. The plant body of this aspect, which is capable of regulating gene expression so that by sugar induction the expression level increases for one or two or more genes selected from among genes coding for sugar-induced storage product-related proteins and transcription factor genes that positively regulate the genes coding for storage product-related proteins as shown in Table 1 below, and the expression level decreases for one or two or more genes selected from among the photosynthesis-related genes as shown in the Table 1.

The present invention provides a plant body production method that may comprise a step of manufacturing a plant body which is capable of repressing expression of one or two or more of first proteins selected from among aforementioned (a1) to (a3) and one or two or more of second proteins selected from among aforementioned (b1) to (b3), the proteins have a sugar-inducible promoter function suppressing activity.

In the method of the present invention, the manufacturing step may includes creating seed by crossing plant individuals in which expression of one of the gene coding for the first protein and the gene coding for the second protein is respectively suppressed. The manufacturing step may include performing genetic manipulation to suppress expression of the gene coding for the protein.

The present invention provides a method of modifying a program for accumulating storage product in a plant body, the method may comprise a step of modifying a plant body to be capable of repressing expression of one or two or more of first proteins selected from among aforementioned (a1) to (a3) and one or two or more of second proteins selected from among aforementioned (b1) to (b3), the proteins having a suppressing activity to suppress function of a sugar-inducible promoter.

The present invention provides a method of producing a plant storage product, the method may comprise a step of producing, in the presence of sugar, a storage product in the plant body of the present invention.

The present invention provides a plant storage product production enhancer that may comprise one or two or more nucleic acid construct, the enhancer suppressing expression of one or two or more of first proteins selected from among aforementioned (a1) to (a3) and one or two or more of second proteins selected from among aforementioned (b1) to (b3).

BRIEF DESCRIPTION OF THE DRAWINGS

FIG. 1 shows the results of sequencing analysis (based on the Clustal W program) on the B3 domain protein family in *A. thaliana*, containing RAV1, RAV2, ARF1, ARF3, ABI3 and HSI2.

FIG. 5 shows a table of the gene groups for which the expression level in the KK strain increased more than 30-fold relative to the wild-type strain when microarray analysis was carried out on the KK strain and the wild-type strain using Agilent Arabidopsis3 oligo Microarrays.

FIG. 6 shows a table of the gene groups for which the expression level in the KK strain decreased to less than $\frac{1}{5}^{th}$ that in the wild-type strain when microarray analysis was carried out on the KK strain and the wild-type strain using Agilent Arabidopsis3 oligo Microarrays.

FIG. 7A shows the expression analysis results by quantitative RT-PCR for transcriptional factor groups which function in seed ripening/embryogenesis as of day 4 or later following the imbibition treatment in wild-type and KK strain seedlings.

FIG. 7B shows the relationship between the group of transcriptional genes that are expressed 5 days after imbibition treatment in wild-type and KK strain seedlings and the culture medium sucrose concentration.

FIG. 8A shows the results of Western blotting analysis on the seed storage protein accumulation state in wild-type and KK-strain seedlings on days 4 to 9 following the imbibition treatment.

FIG. 8B shows the results of FAT RED 7B staining in wild-type and KK strain seedlings on days 5 and 12 following the imbibition treatment.

FIG. 8C shows the analytic results on lipid samples extracted from wild-type and KK strain seedlings on days 4 and 9 following the imbibition treatment.

BEST MODE FOR CARRYING OUT THE INVENTION

Figure 2:
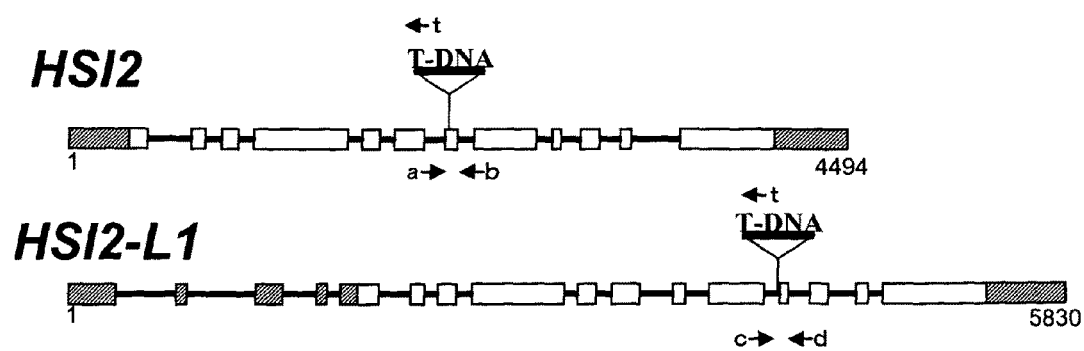
FIG. 2 shows the T-DNA insertion position and the positions of the primers on the HSI2 gene and the HSI2-L1 (HSL1) gene in ΔHSI2 (hsi2-2) and ΔHSI2-L1 (hsl1-1).

The present invention relates to a plant body being constructed so as to be capable of repressing expression of two or more genes coding for two or more proteins, each of the proteins comprises a B3 DNA-binding domain and an EAR motif and has a suppressing activity to suppress function of a sugar-inducible promoter. Having had created plants which are homodeficient for each of the respective genes that encode the two proteins having these characteristics earlier discovered by the inventors (specifically, proteins having a sweet potato sporamin minimal promoter function suppressing activity; more specifically, proteins having the amino acid sequence of SEQ ID NO: 2 or 4), phenotypes in which the genes relating to embryogenesis and the accumulation of storage products are derepressed were found, even though no change whatsoever was observable in the phenotypes of the aforesaid plants homodeficient for one of these genes alone. In other words, these proteins were found to work cooperatively to suppress the expression of genes relating to the embryogenesis and the accumulation of storage products. Therefore, by controlling the expression of these two genes, one should be able to control the operability (period of operation, strength of operation, etc.) of programs for embryogenesis and the accumulation of storage products. For example, it is conceivable that by inhibiting the expression of these two genes, the operation of these programs can be made to begin at other than the normal operating period, or the storage products can be made to accumulate in other than the normal storage organs such as the normal seeds and tubers. Moreover, by inhibiting the expression of these two genes, the embryogenic state is continued. It is thus possible to maintain an undifferentiated state in tissue cultivation (e.g., callus) even without stimulation by plant hormones or the like. The inventive plant body of the present invention thus enables tissue cultivation which both accumulates storage products and has differentiation potency to be readily achieved.

The plant body, plant body production method, method of modifying a program for accumulating storage products in the plant body, method of producing plant storage products, and plant storage product production enhancer serving as different aspect of the invention are described below.

Plant Body

The plant body to which the invention is applied is not subject to any particular limitation, provided it is a higher plant. The invention may be applied to monocotyledons and dicotyledons. In addition to *A. thaliana* used in the working examples of the invention, other exemplary plants include dicotyledons such as soybean, peanut, sesame, rapeseed, cotton, sunflower, safflower (all oil-storing plants), potato and sweet potato (both starch-storing plants), and monocotyledons such as rice, wheat and millet. Of these, dicotyledons are preferred. Plant bodies may be classified as, for example, starch-storing plants, oil-storing plants or protein-storing plants. Of these, the use of oil-storing plants is preferred. Based on the above, preferred plants to which the invention may be applied include oil-storing plants that are dicotyledons, such as peanut, sesame, rapeseed, cotton, sunflower and safflower. Starch-storing plants that are dicotyledons, such as sweet potato and potato, are also preferred. The storage product in the present invention may be, without particular limitation, an oil, a protein or a starch, although an oil is preferred. In addition, aside from storage products intrinsic to the plant body to which the invention is applied, the storage product may be a protein or other substance from another plant or organism which is encoded by a foreign gene and can be produced in the plant.

As used herein, the term "plant body" includes the plant individual, all types and forms of cells capable of constituting the plant individual, tissues and organs which are a part of the plant individual, and generative cells. The phrase "part of a plant individual" encompasses the reproductive media (seeds, tubers, fruit, cut panicles, etc.).

The genes whose expression is to be regulated in the present invention code for proteins which include a B3 DNA-binding domain specific to the plant and an EAR motif, and which have a sugar-inducible promoter function suppressing activity. Here, "sugar-inducible promoter function suppressing activity" means that some protein has an activity which suppresses the operation of a sugar-inducible promoter within the plant body. Moreover, "function suppressing activity" can mean that some protein has an activity which suppresses the expression of a structural gene that has been bonded so as to be capable of activation by a sugar-inducible promoter. Examples of such proteins are exemplified by transcription repression factors which function as active repressors.

The "sugar-inducible promoter" may be a promoter induced by a sugar selected from among monosaccharides, disaccharides and polysaccharides, such as glucose, sucrose or the like which is normally capable of being used by a plant. The sugar is typically sucrose. Known sugar-inducible promoters include At-β Amy (*Arabidopsis thaliana*) (*Plant Physiol* 107, 895-904), ApL3 (*A. thaliana*) (*Plant Physiol* 134, 81-91), and patatin (potato) (*Plant J* 11, 53-62). Examples of sugar-inducible promoters which may serve as indicators for obtaining the protein or gene of the invention include sweet potato sporamin promoter (*Plant Mol Biol.* 14, 595-604; *Plant Physiol* 138, 675-685) (NCBI Accession No.: X13509) and the sweet potato sporamin minimal promoter composed of 210 base pairs (*Mol Genet Genom* 272, 690-699) (SEQ ID NO: 5). The sweet potato sporamin gene encodes a vacuolar protein which is most abundant in tuberous root. The expression of this protein is known to be induced in other plant tissues as well by sugars such as sucrose and glucose. Therefore, when a plant body possesses such a storage product-related sugar-inducible promoter function-suppressing activity, it can be regarded as capable of effectively regulating the embryogenesis program and the storage product accumulation program.

The proteins encoded by the genes whose expression is regulated in the present invention preferably have a B3 DNA-binding domain (Pfam: UK, USA, Accession No: PF02362). Whether or not a given protein has a B3 DNA-binding domain can be determined by the alignment with known B3 DNA-binding domain sequences such as the amino acid sequence of SEQ ID NO: 6 obtained in Accession No. PF02362 at the Pfam web site, or the D3 DNA-binding domain (SEQ ID NO: 30) of VIVIPAROUS1 (Vp1) in *Zea Maize* referenced in *Plant Cell* 9, 799-807 (1997). More specifically, such a determination can be made by using a known pairwise alignment method between an already known B3 DNA-binding domain sequence and the amino acid sequence of a protein which may possibly have a B3 DNA-binding domain (Dot Matrix), a dynamic programming algorithm (Pairs Block Aligner, BCM Search Launcher, etc.) or a word (such as FASTA or BLAST) or k-double method (e.g., BLAST 2 sequence alignment, FASTA program package), or by using a known multiple alignment method between a known B3 DNA-binding domain sequence and a plurality of possible protein amino acid sequences and/or the amino acid sequence of a known B3 DNA-binding domain protein (ClustalW; HAMMER (hidden Markov model), Multi Alin, mkdom/xdom). The proteins that are the targets of regulation have a homology (degree of identity) therebetween of preferably at least 34%, and more preferably at least 76%.

Figure 1:
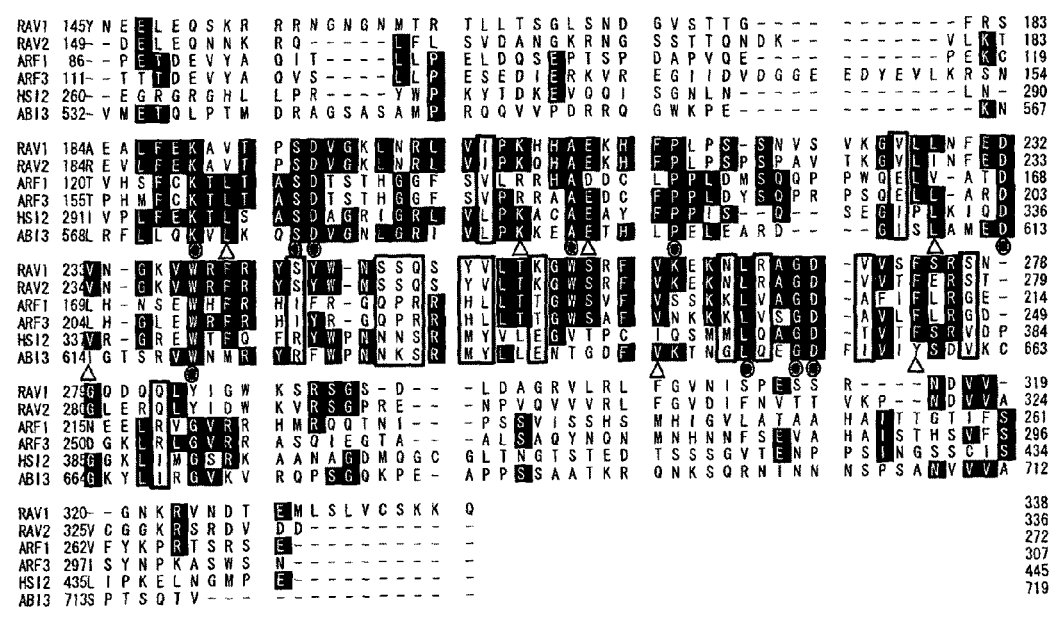

Based on the relationship between HSI2 and other families of this type, the proteins whose expression is regulated in the present invention may contain a B3 DNA-binding domain having the following characteristics. FIG. 1 shows the results of a sequencing analysis (based on the Clustal program) on the B3 domain protein family in *A. thaliana* containing RAV1, RAV2, ARF1, ARF3, ABI3 and HSI2. From this multiple alignment, HSI2 may be said to have the following three characteristics. (1) It has the amino acid residue indicated by the bullet below the amino acid sequence. This amino acid residue is the same in the six proteins. (2) It has amino acids of specific qualities (nonpolar or polar (basic or acidic)) at each of the sites denoted by white triangles. (3) It has amino acid residues preserved between the families at the rectangularly enclosed sites in the diagram. It is desirable for the proteins whose expression is regulated in the invention to have one of these characteristics, and preferably above characteristic (1). The proteins more preferably have at least two of the above characteristics, and even more preferably have all of the above characteristics.

The proteins in the invention preferably have an EAR motif (ERF-associated amphiphilic repression motif) (*Plant Cell* 13, 1959-1968). The EAR motif is on the C-terminus side of the transcription factor proteins. Various types of such EAR motifs have been found, examples of which include those shown in the following table (*Biochem Biophys Res Commun* 321, 172-178; *Trends Plant Sci* 11, 109-112; *Trends Plant Sci.* 11 (3), 109-12 (March 2006)). Sequences which manifest functions similar to these EAR motifs may also be used in the present invention.

TABLE 1

| | core motif | origin organizms | Ptotein name | Function |
|---|---|---|---|---|
| 1 | DLELRL | Arabidopsis | TFIIIA-type zinc-finger protein | |
| 2 | DLDLRL | Arabidopsis | TFIIIA-type zinc-finger protein | |
| 3 | DLTLRL | Arabidopsis | TFIIIA-type zinc-finger protein | |
| 4 | DLSLRL | Arabidopsis | TFIIIA-type zinc-finger protein | |
| 5 | DLSLKL | Arabidopsis | TFIIIA-type zinc-finger protein | |
| 6 | DLSLSL | Arabidopsis | TFIIIA-type zinc-finger protein | |
| 7 | DLSLHL | Arabidopsis | TFIIIA-type zinc-finger protein | |
| 8 | DLTLKL | Arabidopsis | TFIIIA-type zinc-finger protein | |
| 9 | CLDLRL | Arabidopsis | TFIIIA-type zinc-finger protein | |
| 10 | SLDLHL | Arabidopsis | TFIIIA-type zinc-finger protein | |
| 11 | SLDLRL | Arabidopsis | TFIIIA-type zinc-finger protein | |
| 12 | NLNLKL | Arabidopsis | TFIIIA-type zinc-finger protein | |
| 13 | CLDLSL | Arabidopsis | TFIIIA-type zinc-finger protein | |
| 14 | DLNLRL | Zea ramosa | TFIIIA-type zinc-finger protein | * |
| 15 | DLQLRL | Zea ramosa | TFIIIA-type zinc-finger protein | * |
| 16 | DLRLRL | Zea ramosa | TFIIIA-type zinc-finger protein | * |
| 17 | ELELRL | Zea ramosa | TFIIIA-type zinc-finger protein | * |
| 18 | NLELRL | Zea ramosa | TFIIIA-type zinc-finger protein | * |
| 19 | QLELRL | Zea ramosa | TFIIIA-type zinc-finger protein | * |
| 20 | DLELNL | Zea ramosa | TFIIIA-type zinc-finger protein | * |
| 21 | DLELQL | Zea ramosa | TFIIIA-type zinc-finger protein | * |
| 22 | SLELRL | Zea ramosa | TFIIIA-type zinc-finger protein | * |
| 23 | TLELRL | Zea ramosa | TFIIIA-type zinc-finger protein | * |
| 24 | DLELTL | Zea ramosa | TFIIIA-type zinc-finger protein | * |
| 25 | DLELSL | Zea ramosa | TFIIIA-type zinc-finger protein | * |
| 26 | DLHLRL | Zea ramosa | TFIIIA-type zinc-finger protein | * |
| 27 | LDLNL | Arabidopsis | NIMIN1 | Plant defence (salicylic acid signalling) |
| 28 | LDLNV | Rice | NRR | Plant defence (salicylic acid signalling) |
| 29 | LDLNL | Arabidopsis | AtERF4 | Plant defence (jasmonic acid, ethylene and abscisic acid signalling) |
| 30 | FDLNF | Arabidopsis | AtERF7 | Drought stress (abscisic acid signalling) |
| 31 | FDLNL | Arabidopsis | ERF3 | Wound signalling |
| 32 | LDLSL | Arabidopsis | ZAT12 | Cold and oxidative stress |
| 33 | FDLNI | Arabidopsis | ZAT10 | Drought, salt and cold stress |
| 34 | IDLNL | Arabidopsis | AZF2 | Drought stress |
| 35 | LDLNL | Tobacco | NbCD1 | Hypersensitive cell death |
| 36 | PDLNL | Arabidopsis | AtMYB4 | UV stress |
| 37 | LXLXL | Arabidopsis | AUX/IAA | Auxin signalling |
| 38 | IDLNS | Arabidopsis | HSI2 | Sugar signalling |
| 39 | FDLNI | Tobacco | ZFT1 | Spermine signalling |
| 40 | LDLNL | Catharanthus roseus | ZCT1 | Secondary metabolism |
| 41 | LDLNL | Catharanthus roseus | ZCT2 | Secondary metabolism |
| 42 | FDLNL | Catharanthus roseus | ZCT3 | Secondary metabolism |
| 43 | FDLNI | Petunia | ZPT2-3 | Drought tolerance |
| 44 | IDLNSDP | Arabidopsis | B3DNA binding protein HSI2, HSI2-L1 | |
| 45 | LDLNFKP | Arabidopsis | B3DNA binding protein HSI2-L2 | |
| 46 | IDLNSQP | Arabidopsis | B3DNA binding protein OsHSI2 | |
| 47 | IDLNLAP | Arabidopsis | ClassII ERF3 | |
| 48 | FDLNFPP | Arabidopsis | ClassII AtERF3 | |
| 49 | LDLNRPP | Arabidopsis | ClassII OsERF3 | |
| 50 | FDLNIPP | Arabidopsis | Zn-Finger ZAT10 | |

TABLE 1-continued

| | core motif | origin organizms | Ptotein name | Function |
|---|---|---|---|---|
| 51 | IDLNLP | *Arabidopsis* | Zn-Finger ZAT1 | |
| 52 | FDLNIPP | *Arabidopsis* | Zn-Finger WZF1 | |

* includes artificial desgined sequence
1~26 are selected from Biochem. Biophysi. Res. Comu. (321)172-178, 27~43 are selected from Trends Plant Sci. 2006Mar 11(3)109-12, and 44~52 are selected from Plant Pysiol., 2005 June (138)675-685.

The proteins in the invention are exemplified by the following two types of proteins. The first protein is a protein having the amino acid sequence of SEQ ID NO: 2 (HSI2), and the second protein is a protein having the amino acid sequence of SEQ ID NO: 4 (HSI2-L1; HSL1). These proteins are both transcription factor proteins (HSI2 and HSI2-L2 (HSL1)) found to be active repressors of sweet potato sporamin minimal promoters in *A. thaliana*.

Other first proteins include proteins which have an amino acid sequence with, in the amino acid sequence of HSI2, one or more substituted, deleted, inserted and/or added amino acid, and which have an activity of the same nature as HSI2. Other second proteins include proteins which have an amino acid sequence with, in the amino acid sequence of HSI2-L1 (HSL1), one or more substituted, deleted, inserted and/or added amino acid, and which have an activity of the same nature as HSI2-L1 (HSL1). "Activity of the same nature" refers herein to an activity which is identical in nature. The activities may be lower or higher than those of the proteins having the amino acid sequences of SEQ ID NO: 2 and SEQ ID NO: 4, respectively. Such activities can be detected by, for example, having a plant body possessing an expression cassette obtained by binding a suitable reporter gene to a sweet potato sporamin minimal promoter express the protein, and determining whether such reporter gene expression is repressed in the presence of a sugar.

An example of a method for preparing DNA which codes for a protein having a modified amino acid sequence that is familiar to those skilled in the art is the site-directed mutagenesis method (Kramer W & Fritz H-J: *Methods Enzymol* 154, 350 (1987)). Even in the natural world, changes can arise in the amino acid sequence of a protein due to mutations in the base sequence coding for the protein. It is thus desirable for even proteins having an amino acid sequence with, in the amino acid sequence of the natural protein, one or more substituted, deleted, inserted and/or added amino acid, to have an activity of the same nature as the amino acid sequence of SEQ ID NO: 2 or 4.

Examples of other first proteins include proteins which are coded by DNA that hybridizes under stringent conditions to DNA having the base sequence of SEQ ID NO: 1 or to a part of a complementary strand thereto, and which have an activity of the same nature as HSI2. Examples of other second proteins include proteins which are coded by DNA that hybridizes under stringent conditions to DNA having the base sequence of SEQ ID NO: 3 or to a part of a complementary strand thereto, and which have an activity of the same nature as HSI2-L1 (HSL1). The base sequence of SEQ ID NO: 1 is a base sequence which codes for HSI2, and the base sequence of SEQ ID NO: 3 is a base sequence which codes for HSI2-L1 (HSL1).

Methods for obtaining such other proteins include techniques involving the use of hybridization (Southern E M: *J Mol Biol* 98, 503 (1975)) or the polymerase chain reaction (PCR) (Saiki R K, et al: *Science* 230, 1350 (1985); Saiki R K, et al.: *Science* 239, 487 (1988)). That is, obtaining such a protein by using as the probe DNA which codes for a protein having the amino acid sequence of HSI2 or a protein having the amino acid sequence of HSI2-L1 (HSL1), or a portion of such DNA or a complementary strand thereof, or by using as the primer an oligonucleotide which hybridizes specifically with the base sequence of genomic DNA for such a protein, in order to isolate from *A. thaliana* or some other plant DNA which codes for protein having an activity of the same nature as HSI1 or HSI2-L1 (HSL1) is within a range that can be ordinarily carried out by persons skilled in the art.

DNA coding for such a protein may preferably be obtained by carrying out a hybridization reaction under stringent conditions. In the present reaction, "stringent hybridization conditions" refers to the hybridization conditions 6 M urea, 0.4% SDS, 0.5×SSC, or hybridization conditions of comparable stringency. Under conditions of higher stringency, such as 6 M urea, 0.4% SDS and 0.1×SSC, it is expected that DNA having a higher homology can be isolated. "High homology" refers herein to a sequence homology which, over the entire amino acid sequence, is at least 50%, preferably at least 70%, more preferably at least 90%, and most preferably at least 95%.

The homology of the amino acid sequence or base sequence can be determined using the algorithm BLAST created by Karlin and Altschul (*Proc. Natl. Acad. Sci. USA* 87, 2264-2268 (1990); *Proc. Natl. Acad. Sci. USA* 90, 5873 (1993)). Programs called BLASTN and BLASTX have been developed based on the BLAST algorithm (Altschul SF, et al.: *J Mol Biol* 215, 403 (1990)). Specific techniques for these methods of analysis are commonly known.

The plant body of the invention is constructed in such a way that expression of a gene coding for HSI2 or a protein substantially identical to HSI2 or a gene coding for HSI2-L1 (HSL1) or a protein substantially identical to HSI2-L1 (HSL1) can be repressed. Here, the gene coding for HSI2 or a protein substantially identical to HSI2 or for HSI2-L1 (HSL1) or a protein substantially identical with HSI2-L1 (HSL1) includes genes that are normally present in the plant body, as well as genes that are retained on a chromosome by some means such as gene manipulation, crossing or mutation. In the plant body of the invention, so long as the expression of both a gene coding for the first protein and a gene coding for the second protein is repressed, the repressed proteins may be merely one of each type or may be a combination of two or more of each type.

Various techniques may be used to construct a plant body in which the expression of two or more genes is repressed in this way. In the invention, "repressing the expression of a gene" encompasses repressing gene transcription, repressing translation to a protein and the expression of incomplete proteins. In all of these forms, aside from complete repression or mutation, partial repression or mutation within a range capable of modifying operation of the embryogenesis program or storage protein accumulation program is acceptable. The plant body in which gene expression is repressed may be the entire plant body or a portion thereof.

The method of repressing the expression of two or more specific genes in the plant may involve, for example, crossing or gene manipulation. Plant bodies obtained by crossing are plant bodies obtained by natural or artificial fertilization and seed formation between plants deficient for one or two or more genes. Plant bodies obtained by genetic manipulation are plant bodies regenerated from plant cells in which specific genes have been knocked out, or from plant cells in which a nucleic acid construct capable of repressing expression targeted at mRNA has been introduced and retained using, for example, an antisense, cosuppression, RNA interference or ribozyme method. In the present invention, the repression of gene expression by a cause present within the target gene due to, for example, defect or mutation of the target gene by crossing, knockout or the like is referred to as the repression of gene expression by an intrinsic factor, and the repression of gene expression by a cause other than one present in the target gene due to an antisense, cosuppression, RNA interference, ribozyme or other method is referred to as the repression of gene expression by an extrinsic factor. Techniques that may be used in the invention to repress the expression of two or more genes are not limited to the methods mentioned above.

The antisense method may repress gene expression by any of a number of actions, such as inhibiting the start of transcription due to triplex formation, inhibiting transcription, and inhibiting splicing. Examples include an antisense sequence complementary to a nontranslational region near the 5' end of the gene mRNA, an antisense sequence complementary to a coding region or to a nontranslational region on the 3' side, and an antisense sequence on a nontranslational region sequence. DNA coding for such an antisense sequence can be introduced into the plant body by a known method in a form that is ligated downstream from a promoter, and preferably where a sequence containing a transcription termination signal is coupled to the 3' side. The antisense DNA sequence is preferably a sequence which is complementary to an intrinsic gene of the plant to be transformed, or a portion of such an intrinsic gene, although complete complementarity is not essential so long as gene expression can be effectively repressed. The transcribed RNA has a complementarity with respect to the target gene transcription product of preferably at least 90%, and most preferably at least 95%. To effectively repress expression of the target gene using an antisense sequence, it is desirable for the antisense sequence to have a length of at least 15 bases, preferably at least 100 bases, and more preferably at least 500 bases.

The RNA interference (RNAi) method, in order to repress expression of the DNA of the present invention in the plant body by RNAi, is able to use DNA of the invention (e.g., the DNA of SEQ ID NO: 1 or 3) or two-stranded RNA having a sequence similar thereto (Chuang C F & Meyerowitz E M: *Proc. Natl. Acad. Sci. USA* 97, 4985 (2000)). The gene used in the RNAi method does not need to be exactly identical to the target gene, although it is desirable for the sequence homology to be at least 70%, preferably at least 80%, more preferably at least 90% and most preferably at least 95%. The sequence homology can be determined by the above-described technique.

Cosuppression is a suppression of expression by a target gene that arises due to the transformation of DNA having a sequence which is the same as or similar to the target gene sequence. Cosuppression is even observed in plants (Smyth D R: *Curr Biol* 7, R793 (1997); Martienssen R: *Curr Biol* 6, 810 (1996)). For example, to obtain a plant body in which expression of the DNA of the invention has been repressed by cosuppression, vector DNA created so as to be able to express the DNA of the present invention (e.g., the DNA of SEQ ID NO: 1 or 3) or DNA having a sequence similar thereto is transformed to the target plant, following which the resulting plant bodies are compared with wild-type plant bodies and those plants in which root elongation has been suppressed are selected. The gene used in cosuppression need not be exactly identical to the target gene, although it is desirable for the sequence homology to be at least 70%, preferably at least 80%, more preferably at least 90%, and most preferably at least 95%. The homology of the sequence can be determined by the technique described above.

In the ribozyme method, although there also exist large ribozymes composed of more than 400 nucleotides, such as group I intron ribozyme and the M1 RNA within RNase P, use may be made of the active domains composed of about 40 nucleotides known as the hammerhead ribozyme and the hairpin ribozyme (Koizumi M and Otsuka E: *Tanpakushitsu Kakusan Koso* (Protein Nucleic Acid and Enzyme)) 35, 2191 (1990)). Sequences which function as a hammerhead ribozyme or a hairpin ribozyme may be used (Koizumi M, et al.: *FEBS Lett* 228, 228 (1988); Koizumi M, et al.: *FEBS Lett* 239, 285 (1988); Koizumi M and Otsuka E: *Tanpakushitsu Kakusan Koso* (Protein Nucleic Acid and Enzyme) 35, 2191 (1990); Koizumi M, et al.: *Nucl Acids Res* 17, 7059 (1989); Buzayan J M: *Nature* 323, 349 (1986); Kikuchi Y & Sasaki N: *Nucl Acids Res* 19, 6751 (1991); Kikuchi Y: *Kagaku to Seibutsu* (Chemistry and Biology) 30, 112 (1992)). DNA coding for a ribozyme can be introduced into the plant body by linking it to, for example, a promoter such as the 35S promoter of the cauliflower mosaic virus and a transcription termination sequence (Taira K, et al.: *Protein Eng* 3, 733 (1990); Dzianott A M & Bujarski J J: *Proc Natl Acad Sci USA* 86, 4823 (1989); Grosshans C A & Cech T R: *Nucl Acids Res* 19, 3875 (1991); Taira K, et al.: *Nucl Acids Res* 19, 5125 (1991)).

The plant body of the present invention is constructed so as to repress or be capable of repressing the expression of the genes coding for the above proteins. This plant body of the invention is able to increase the level of expression of sugar-induced late embryogenesis genes. In *A. thaliana*, an increase in the level of expression of such genes is observed; on account of this form of expression, an embryogenic state forms, which appears to promote the synthesis and accumulation of storage products in seeds, etc. The plant body of the invention is also able to increase the level of expression by genes coding for sugar-induced storage product-related proteins and by transcription factor genes that positively regulate genes coding for such storage product-related proteins, while at the same time reducing the level of expression of photosynthesis-related genes. Such expression trends are observed in *A. thaliana*. Owing to this form of expression, it appears that the synthesis and accumulation of storage products is promoted in the presence of sugar.

In a case where the plant body of the invention is all or part of a plant individual, in one embodiment, the plant body accumulates a storage product such as an oil at a site other than the normal storage organ under sugar induction. For example, the plant body may be a seedling individual which accumulates the storage product in the hypocotyl. Furthermore, in the case with the plant body being a seed, which is a reproductive material, it may accumulate a storage product such as oil in the hypocotyl of the seedling individual under sugar induction following germination. In a case where the plant body of the invention is cultivated tissue such as a callus, because propagation can be carried out while maintaining an embryogenic state, use in a tissue culture or cell culture that produces the storage product is possible.

When the plant body of the invention is *Arabidopsis thaliana* or is derived from this plant species, gene expression can be regulated in such a way that the level of expression of genes coding for sugar-induced storage product-related proteins and of transcription factor genes that positively regulate genes coding for such storage product-related proteins increases, which genes are shown in Table 1, and the level of expression of photosynthesis-related genes shown in the table decreases. It is thus possible to promote the production of proteins encoded by these genes and of products synthesized with these proteins. In addition, by using a nucleic acid construct in which genes coding for extrinsic proteins are ligated downstream from the promoters for these genes, it is also possible to have proteins or other products from other plant bodies or organisms be expressed in the plant body.

Method of Producing a Plant Body, and Method of Modifying a Program for Accumulating Storage Product in a Plant Body The method herein of producing the plant body includes the step of manufacturing a plant body which is capable of repressing the expression of the above-mentioned two or more genes, which manufacturing step is carried out, as described above, by crossing plant individuals or by genetic manipulation. Furthermore, the method herein of modifying a program for accumulating a storage product in a plant body includes a step in which a plant body which is capable of repressing the expression of the above-mentioned two or more genes is modified, which step is part of the above manufacturing step that is carried out in the foregoing method of producing a plant body. The plant body modifying step includes a step in which crossing or genetic manipulation are only carried out within a range where seeds or plant individuals are not ultimately regenerated by such crossing or genetic manipulation.

The step of manufacturing the plant body of the present invention by crossing is a step in which plant bodies having defects or mutations at one or two or more genes are crossed, and the seeds thereof are obtained. The step of manufacturing the plant body of the present invention by gene manipulation is a step that involves building a nucleic acid construct capable of repressing the expression of two or more genes (such as by a knockout, antisense, RNAi, ribozyme or cosuppression method), introducing the construct into plant cells, and regenerating the plant body from the plant cells. Vectors which may be used to transform the plant cells are not subject to any particular limitation, provided they have the ability to express the inserted gene within the cell. For example, use may be made of a vector having a promoter for constantly expressing the gene within the plant cells (e.g., the 35S promoter of the cauliflower mosaic virus), or a vector having a promoter which is inductively activated by an external stimulus.

The cell into which the nuclei acid construct is introduced includes all types of plant cells which are capable of regeneration into a plant body. Illustrative examples include sections of specific organs, such as cultured cells, protoplasts, shoot primordia, polyblasts, capillary roots, calluses or leaves. By carrying out a specific regeneration step, the plant transformant is able to transform the cell into a plant body. Although the method of regeneration differs with the type of plant, various known methods may be used.

Any of various methods known to those skilled in the art, such as the polyethylene glycol method, electroporation, an agrobacterium-mediated method or the particle gun method may be used to introduce the nucleic acid construct into the plant cells. In the particle gun method, use may be made of the system available from Bio-Rad Laboratories. Regeneration of the plant body from a transformant cell may be carried out by a method known to those skilled in the art, in accordance with the type of plant cell. Also, progeny may be obtained from the regenerated plant body by sexual or asexual reproduction. Moreover, it is possible to obtain reproductive materials (e.g., seeds, fruit, cut panicles, tubers, tuberous roots, rootstock, calluses, protoplast) from such plant bodies and their progeny, or clones thereof, and mass produce such plant bodies based on these.

A number of techniques have already been established and are in wide use in the technical field of the invention. For example, techniques for creating transformed plant bodies in *A. thaliana* include the vacuum method (Bechtold, N. & Pelletier, G: *Methods Mol. Biol.* 82, 259-266 (1998)) and the floral dip method (Clough, S. J. & Bent, A. F.: *Plant J.* 16, 735-743 (1998)), and techniques for creating transformed plant bodies in poplar include a method which uses Agrobacterium (Leple, J. C. et al.: *Plant Cell Rep.* 11, 137-141 (1992)). Techniques for creating transformed plant bodies in rice include a method that involves introducing a gene into a protoplast using polyethylene glycol, and regenerating a plant body (indica type rice varieties are suitable) (Datta S K: in *Gene Transfer to Plants* (Potrykus I and Spangenberg, Eds), pp. 66-74 (1995)); a method that entails introducing a gene into protoplast by electrical pulses, and regenerating a plant body (japonica type rice varieties are suitable) (Toki S, et al.: *Plant Physiol* 100, 1503 (1992)); a method which involves introducing a gene directly into a cell by the particle gun technique, and generating a plant body (Christou P, et al.: *Biotechnology* 9, 957 (1991)), and a method that involves introducing a gene via Agrobacterium, and regenerating a plants body (Hiei Y, et al.: *Plant J* 6, 271 (1994)). Advantageous use of these methods may be made in the present invention.

Method of Producing Plant Storage Products

In the plant body of the invention, by repressing the expression of the above-mentioned two or more genes, the embryogenesis program or the storage product accumulation program is initiated under sugar induction. With the initiation of these programs, at least embryogenesis is initiated and maintained or the synthesis and accumulation of storage products is initiated and maintained. As shown in the subsequently described examples, in *A. thaliana*, embryogenesis and oil synthesis and accumulation are initiated at the time of germination. In a callus culture, together with oil synthesis and accumulation, an embryogenic state can be maintained even without plant hormone stimulation. Accordingly, plant storage products can be produced by growing or propagating the plant body of the invention.

Plant Storage Product Production Enhancer

The plant storage product production enhancer of the invention is a nucleic acid construct which represses the expression of the above described two or more genes. As already explained above, such a nucleic acid construct is introduced into the plant body by genetic manipulation so as to obtain a transformed plant body, and is thus able to promote the accumulation and production of plant storage products.

EXAMPLES

The invention is described more fully below in the following examples, which are illustrative and should not be construed as limiting the invention.

First, the materials and methods used in the following examples are described.

Materials and Methods

1. Plant Materials

Mouse-ear cress (*Arabidopsis thaliana* (L.) Heynhold, Col-0 ecotype; referred to below simply as "wild type") was used as the plant material. The mutant line ΔHSI2 (hsi2-2)

from a wild type background was acquired from the Arabidopsis Biological Resource Center (ABRC) at the SALK Institute (La Jolla, Calif.). In addition, ΔHSI2-L1 (hsl1-1), which is a transformed line (SALK_059568) obtained by inserting T-DNA in the No. 12 exon of the HSI2-L1 (HSL1) gene, was acquired from the SALK Institute.

2. Growing the Plants

The surfaces of the seeds were sterilized with a sterilizing solution composed of 0.025% TritonX-100 and 5% NaClO and rinsed from 3 to 5 times with sterilized water, following which, unless noted otherwise, the seeds were sown on a plate containing a medium of Gamborg B-5 vitamin (100 mg/L myoinositol, 10 mg/L thiamine hydrochloride, 1 mg/L nicotinic acid, 1 mg/L pyridoxine hydrochloride; Gamborg et al., 1968), 2.5 mM Mes-KOH (pH 5.7 to 5.8), 1% sucrose-containing MS inorganic salt (Murashige and Skoog, 1962) to which 0.3% gellite was added for solidification. To break the dormancy of the seeds, following 2 to 5 days of incubation at 4° C. in the dark, the seeds were transferred to a growth cabinet (Sanyo) at 22° C. under continuous lighting at an intensity of 40 to 50 E/m2s and grown.

To obtain progeny seed, plants grown for about two weeks on the plate were transferred to a pot containing vermiculite, and grown in a plant growth cabinet (Sanyo) at 22° C. and under continuous lighting. Hyponex (Hyponex Japan) diluted from 2,000 to 5.000-fold with tap water was suitably applied as liquid fertilizer.

A medium prepared by adding 0.86 μM indoleacetic acid (IAA) and 2.5 μM $N^6$-($\Delta^2$-isopentenyl)-adenine (2iP) to a basic medium was used as a shoot-inducing medium (SIM). A medium prepared by adding 2.3 μM 2,4-dichlorophenoxyacetic acid (2,4D) and 0.46 μM kinetin to a basic medium was used as a callus-inducing medium (CIM).

3. Examination of Plant Body Sections

An entire seedling on day 5 following an imbibition treatment was fixed with a water/ethanol/acetic acid/formalin solution (20:18:1:1, v/v) FAA for 16 hours at 4° C., then dehydrated by increasing the ethanol concentration in stages. Next, the sample was encapsulated using Technobit 7100 (Kulzur Wehrheim, Germany), in accordance with the protocol provided. The encapsulated sample was sectioned to a thickness of 0.5 μm using an RM2125RT rotary microtome (Leica; Wein, Austria) equipped with a tungsten knife, and the sections were dried on cover glasses. The sections were then stained with 0.05% Toluidine Blue (Merck; Darmstadt, Germany) for 1 minute at room temperature, following which they were promptly rinsed with water for 5 minutes, and examined under a microscope (BX60; Olympus, Tokyo).

4. Genotyping of T-DNA Insertion Mutant Line

The extraction of genomic DNA for genotyping and the determination of T-DNA insertion sites in Δhsi2 (hsi2-2) and Δhsi2-L1 (hsl1-1) were carried out as follows.

4-1. Genomic DNA Extraction

The genomic DNA was extracted by placing one leaf cut from the plant body into a microtube (Yasui Kikai) in which 40 μL of 0.4 N NaOH had been placed, adding a magnetic metal cone, and carrying 5 seconds of disruption twice in a Multibead Shocker (Yasui Kikai). The disruptate was neutralized by adding 200 μL of 100 mM Tris-HCl (pH 8.0), then centrifuged at 4° C. and 2,000 rpm. The resulting supernatant was used as the genomic DNA solution in the PCR reaction. Genomic DNA for DNA sequencing was extracted by the CTAB method, thereby increasing the purity of the template DNA in PCR reaction. That is, 2 g of the plant body was disrupted by freezing, after which 5 mL of CTAB buffer (1.42 M NaCl, 20 mM EDTA (pH 8.0), 100 mM Tris-HCl (pH 8), 0.25 mM polyvinylpyrrolidone, 52.9 mM cetyl trimethyl ammonium bromide) was added and the mixture was incubated at 55° C. for 30 minutes. Next, 5 mL of chloroform was added and the sample was immersed therein at room temperature for 30 minutes, following which 10 minutes of centrifugation was carried out at 3,000 rpm. The resulting supernatant was used as a pure DNA solution in a PCR reaction.

4-2. Determination of T-DNA Insertion Sites in T-DNA Insertion Mutant Strains ΔHSI2 (hsi2-2) and ΔHSI2-L1 (hsii-1)

Genomic DNA was extracted by a method that used the above-mentioned Bead Shocker, following which determinations of the T-DNA insertion sites in the T-DNA insertion mutant strains ΔHSI2 (hsi2-2) and ΔHSI2-L1 (hsl1-1) were carried out using a HSI2 gene specific primer, an HSI-L1 (HSL1) gene specific primer and a T-DNA specific primer. FIG. 2 shows the T-DNA insertion sites and the positions of the primers on the HSI2 gene and the HSI2-L1 (HSL1) gene.

The primer sets a to d had the following structures. Determinations of the T-DNA insertion sites on the HSI2 gene and the HSI2-L1 (HSL1) gene were carried out by DNA sequencing (separately described) PCR products obtained using, respectively, primer set b and primer set d.

```
Primer set a:
S08-f;
5'-GTATCACCAGCCTGTAGCATCATGGAC-3'    (SEQ ID NO: 7)

S08-r;
5'-AGGCAGCTAATGCTGGAGACATGCAG-3'     (SEQ ID NO: 8)

Primer set b:
S08-f;
5'-GTATCACCAGCCTGTAGCATCATGGAC-3'    (SEQ ID NO: 7)

PL11;
5'-TTTCGCCTGCTGGGGCAAACCAG-3'        (SEQ ID NO: 9)

Primer set c:
S054;
5'-AAGCATCACACTGCACCCATTGCT-3'       (SEQ ID NO: 10)

S05-r;
5'-TCGGAACATTGGGACTAAGAGCAAG-3'      (SEQ ID NO: 11)

Primer set d:
S05-f;
5'-AAGCATCACACTGCACCCATTGCT-3'       (SEQ ID NO: 10)

PL11;
5'-TTTCGCCTGCTGGGGCAAACCAG-3'        (SEQ ID NO: 9)
```

In the DNA sequencing performed to elucidate T-DNA insertion site determinations, a Big Dye Terminator Cycle Sequencing Kit v3.1 (available from Applied Biosystems) was used to carry out the sequencing reactions and a Capillary Sequencer ABI Prism 3100 (available from the same company) was used to determine the DNA sequences of the sequencing reaction products by electrophoresis.

6. Microarray Analysis

Total RNA was extracted from wild-type and KK line seedling plants on day 4 following the imbibition treatment, following which Cy3- and Cy5-labeled cRNA probes were prepared using Agilent's Low RNA Input Fluorescent Linear Amplification Kit (Agilent Technology; Palo Alto, Calif.) in accordance with the protocol provided, and hybridization with Agilent Arabidopsis3 oligo Microarray was carried out. In microarray analysis, hybridization was carried out for each of two independent RNA extracts. Signal detection, analysis and normalization following the total of two hybridizations were carried out using Feature Extractor (Version A.7.5.1; Agilent Technology). Raw data on the microarrays and details on the cRNA labeling and hybridization experiments were registered with the public microarray database Arrayexpress under Accession No. E-MEXP-542 (although this data was not yet open to the public at the time the present patent application was filed).

7. Expression Analysis by Quantitative RT-PCR

Single-stranded cDNA for quantitative real-time polymerase chain reaction (RT-PCR) was prepared by SUPER-SCRIPT III (Invitrogen) using an oligo(dT) 20 primer from 5 µg of total RNA, then diluted 10-fold with Rnase-free water. RT-PCR was carried out in 25 µL of reaction solution with 5 µL of diluted cDNA template solution, 12.5 µL of Cybergreen dye set mixed solution (Bio-Rad) and 0.5 µL each of the gene-specific primers (final concentration, 200 nM). The reaction was carried out under the following conditions: 95° C., 5 minutes (15 seconds at 95° C., 15 seconds at 60° C., 30 seconds at 72° C.), 40 cycles. The relative mRNA level was calculated based on the Ct method. ACT2 was used as the internal standard gene. The primer sets used in each reaction are shown below. The sequences cited in Mendoza et al. (2005) were used for oleosin S3, At2S3, LEC1 and LEC2.

```
ACT2-
Forward;
5'-CTGTTGACTACGAGCAGGAGATGGA-3'    (SEQ ID NO: 12)

Reverse;
5'-GACTTCTGGGCATCTGAATCTCTCA-3'    (SEQ ID NO: 13)

HSI2
Forward;
5'-CTTCCATATCAGCTTGAAACTCTC-3'     (SEQ ID NO: 14)

Reverse;
5'-TGGCTCAAGACGCCAGTGATGTTT-3'     (SEQ ID NO: 15)

HSI2-L1(HSL1)
Forward;
5'-ATGAGGCTTCTCCAAGCTGCAGCGT-3'    (SEQ ID NO: 16)

Reverse;
5'-GAACCGTGTTCTGTGCTGACCATAT-3'    (SEQ ID NO: 17)

LHCB2:4
5'-GTAA AGGT CCGA TCGA AAAT CTGT-3' (SEQ ID NO: 18)

5'-TTAT CCGA TCAA ACTC TATT TTCCG-3' (SEQ ID NO: 19)

Oleosin S3
Forward;
5'-AGGCAGATTGCTAAAGCTGCAAC-3'      (SEQ ID NO: 20)

Reverse;
5'-ACTGTGATGAGAGCCGGG-3'           (SEQ ID NO: 21)

At2S3
Forward;
5'-AGCAAAACATGGCTAACAAGCTCT-3'     (SEQ ID NO: 22)

Reverse;
5'-CTGGCATCTCTGTCTTGGACCT-3'       (SEQ ID NO: 23)

LEC1
Forward;
5'-ACCAGCTCAGTCGTAGTAGCC-3'        (SEQ ID NO: 24)

Reverse;
5'-GTGAGACGGTAAGGTTTTACGCATGAT-3'  (SEQ ID NO: 25)

LEC2
Forward;
5'-CTCTCTCTCTCTCCGGGAAA-3'         (SEQ ID NO: 26)

Reverse;
5'-CCATCTGCTCCACCGGGTAT-3'         (SEQ ID NO: 27)

WRI1
Forward;
5'-TCTTTGGGACAAAAGCTCTTGGAATTCGAT-3' (SEQ ID NO: 28)

Reverse;
5'-TACGTATGTGCTGCTGCTTCTIVACT-3'   (SEQ ID NO: 29)
```

8. SDS-PAGE and Western Blotting

SDS-Polyacrylamide Gel Electrophoresis (SDS-PAGE) and Western blotting using oleosin S4 and 12S Globulin antibodies were carried out in accordance with Shimada et al. (*J. Biol. Chem.* 278, 32292-32299 (2003)). Wild-type dry seeds, seedlings and detached hypocotyls were disrupted in an extraction buffer containing 50 mM Tris-HCl (pH 8.0), 0.05% SDS, 5% mercaptoethanol and 10% glycerol. The disruptate was incubated at 95° C. for 5 minutes, then centrifuged at 15,000 rpm for 10 minutes. The supernatant was submitted to SDS-PAGE and subsequently transferred to a polydifluorovinylidene membrane (0.45 mm; Nihon Millipore, Tokyo) using a semidry-type transfer apparatus (Bio-Rad Laboratories). The membrane following transfer was incubated in a 5% (w/v) skim milk-containing buffer of 20 mM Tris-HCl (pH 7.5), 0.14 M NaCl and 0.05% (w/v) Toriton-X100, then incubated for 1 hour in anti-12S globulin antibody (20.000-fold dilution) or anti-oleosin S4 antibody (10.000-fold dilution). Next, horseradish peroxidase-labeled anti-rabbit IgG antibody (5.000-fold dilution; GE Healthcare Bio-Science; Piscataway, N.J.) was used as a secondary antibody. Signals were detected using ECL Western Blotting Detection Reagent (GE Healthcare Bio-science).

9. Fat Red 7B Staining

Tissue staining using Fat Red 7B was carried out in accordance with the method of Brundrett et al. (1991). Fat Red 7B (0.1% (w/v); Sigma) was dissolved in polyethylene glycol (average molecular weight, 400 D, Sigma; St. Louis, Mo.) for 1 hour at 90° C., then mixed with an equal volume of 90% (v/v) glycerol, and the resulting mixture was used as the staining solution. The tissue sample in this staining solution was incubated for 1 hour at room temperature. Next, it was rinsed several times with water, after which it was mounted on a slide glass with glycerol and examined under a microscope (SZX12, OLYMPUS).

10. Lipid Analysis

To analyze triacylglycerol (TAG), 20 mg of tissue was disrupted in 1 mL of a chloroform/methanol mixture (2:1, v/v), and centrifuged at 15,000 rpm for 5 minutes. The supernatant was evaporated to dryness, then re-dissolved in 20 µL of chloroform. This lipid sample was spotted onto a silica gel 60F254 HPTLC sheet (Merck) and developed using hexane/diethyl ether/acetic acid mixture (4:1:0.05, v/v) as the developing solvent. Pure glycerol trilinolenic acid (Sigma) was developed at the same time as a TAG standard sample. Sulfuric acid was coated onto the HPTLC sheet following development, following which the sheet was heated at 120° C. for 5 minutes to visualize the lipid.

Example 1

Isolation of Double Knockout Mutant Strains of HSI2 and HSI2-L1 (HSL1)

A T-DNA homoinsertion line was selected by genomic PCR from a mutant line (SALK_059568) obtained by inserting T-DNA at the No. 12 exon of the HSI2-L1 (HSL1) gene. Compared with the wild type, the homoinsertion line had a markedly lower amount of HSI2-L1 (HSL1) mRNA. Based on this result, the T-DNA insertion mutant line was called ΔHSI2-L1 (hsl1-1). ΔHSI2-L1 (hsl1-1) plant bodies had no conspicuous anomalies and exhibited growth similar to that of the wild-type strain.

Next, F1 seeds obtained by crossing a ΔHSI2 (hsi2-2) homo line plant with a ΔSI2-L1 (hsl1-1) homo line plant were allowed to self-pollinate, giving F2 plants, from which F3 plants were subsequently obtained. Of the 144 F3 plants obtained, eight individuals were abnormal seedlings which stopped growing in 9 days. This implied that double mutants for ΔHSI2 (hsi2-2) and ΔHSI2-L1 (hsl1-1) are abnormal seedlings. Hence, Δhsi2$^{-/-}$/Δhsi2-11$^{+/-}$ and Δhsi2$^{+/-}$/Δhsi2-11$^{-/-}$ genotype plants were selected by genomic PCR, and respectively allowed to self-pollinate, giving the offspring plants. In the former, 62 out of 252 individuals ($X^2$ value for 3:1 ratio=0.085, p≧0.05) exhibited abnormal phenotypes, and in the latter, 35 out of 134 individuals ($X^2$ value for 3:1 ratio=0.09, p ≧0.05) exhibited abnormal phenotypes. The genotype of the abnormal seedlings was Δhsi2$^{-/-}$/Δhsi2-11$^{-/-}$; hence, when a plant had at least one wild-type HSI2 or HSI2-L1 (HSL1), it grew normally in the same way as a wild-type plant.

Figure 3:
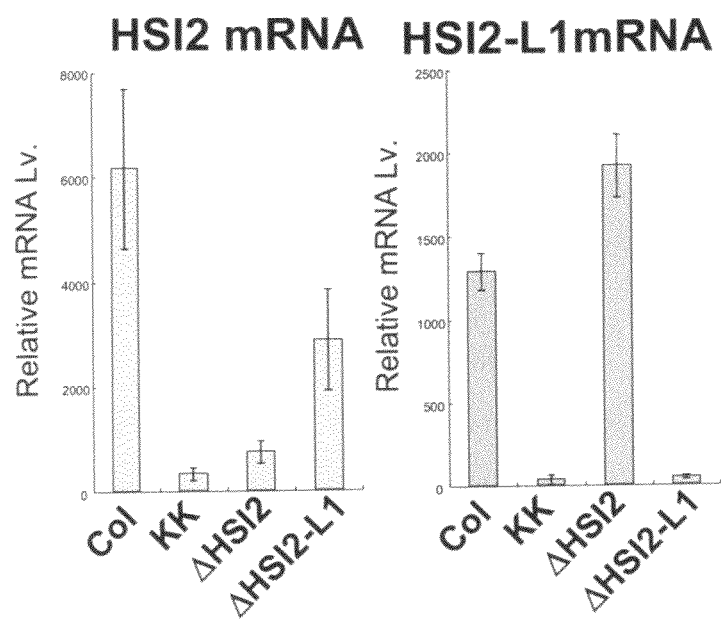
FIG. 3 shows the results of mRNA determinations by real-time PCR for wild-type (Col), KK strain, $\Delta hsi2^{-/-}/\Delta hsi2\text{-}11^{+/-}$ strain and $\Delta/hsi2^{+/-}/\Delta hsi2\text{-}11^{-/-}$ strain.

FIG. 3 shows the results obtained when RT-PCR was carried out on these mutants and the amount of mRNA was determined. As shown in FIG. 3, in a double mutant (KK strain) having the genotype Δhsi2$^{-/-}$/Δhsi2-11$^{-/-}$, given that the quantities of HSI2 mRNA and HSI2-L1 (HSL1) mRNA were both very small, the amount of these genes transcribed was found to have greatly decreased. Because the frequency with which abnormal seedlings arose was about the same in the offspring of Δhsi2$^{-/-}$/Δhsi2-11$^{+/-}$ and Δhsi2$^{+/-}$/Δhsi2-11$^{-/-}$, the abnormal seedling phenotypes did not appear to be due to mutations of genes other than HSI2 and HSI2-L1 (HSL1). From the above, the abnormal seedling phenotypes in the KK strain appear to be due to a decrease in the level of expression of HSI2 and HSI2-L1 (HSL1), judging from which HSI2 and HSI2-L1 (HSL1) appear to mutually complement the functions essential for growth of the seedlings.

Example 2

Detailed Analysis of the Phenotypes of Double Mutant Strains

Figure 4:
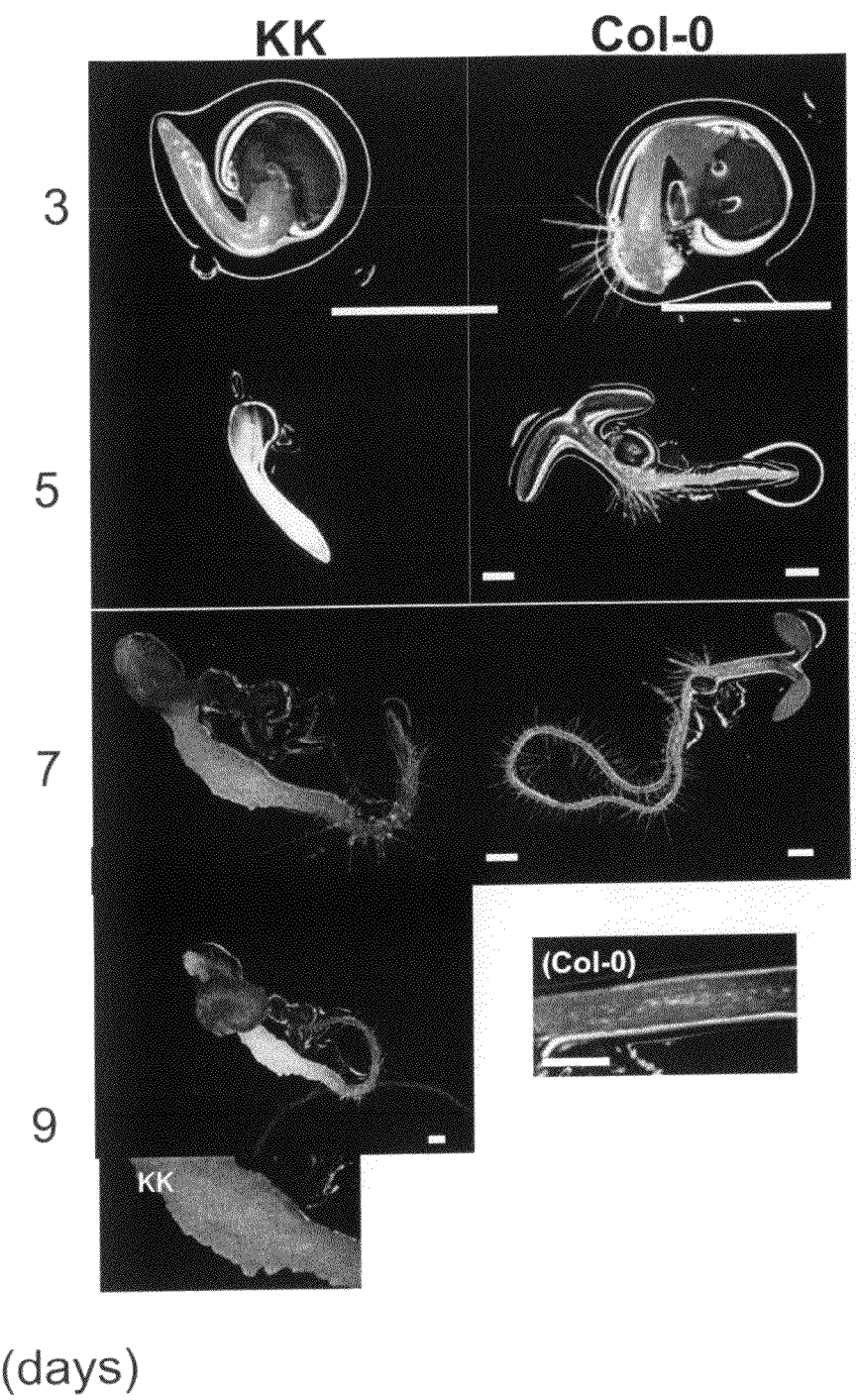
FIG. 4 shows the results (photographs) of phenotype analysis on the KK strain. The photographs in the left-hand column are of the KK strain and the photographs in the right-hand column are of the wild-type strain. The numbers on the left side of the photographs in the left-hand column indicate the number of days elapsed following an imbibition treatment.

To observe the growth of double mutant strain seedlings, Δhsi2$^{-/-}$/Δhsi2-11$^{+/-}$ and Δhsi2$^{+/-}$/Δhsi2-11$^{-/-}$ progeny plant seeds were germinated in a 1% sucrose-containing agar medium. In wild-type A. thaliana, root hairs developed on day 3 after imbibition treatment (FIG. 4, top row in right-hand column), a green cotyledon opened up on day 5 (FIG. 4, second row in right-hand column), and the roots elongated a considerable degree on day 7 (FIG. 4, third row in right-hand column). Also, surface unevenness was not observed in the wild-type hypocotyls (FIG. 4, bottom row in right-hand column). By contrast, in the KK strain, because a distinctive retardation of the development of the root hairs and the opening of the cotyledon were observed (FIG. 4, top row and second row in left-hand column), these seedlings were distinguishable from seedlings of other genotypes on days 3 to 5 after imbibition treatment. Also, in the KK strain, on day 5 following the imbibition treatment, the hypocotyls thickened (FIG. 4, row 2 in left-hand column); on day 7 following the imbibition treatment, the hypocotyls became light yellow in color and came to acquire an uneven surface (FIG. 4, row 3 in left-hand column). Also, on day 9, the thickened, uneven-surfaced hypocotyls became yellow in color and callus-like, along with which growth in most of the KK strain had stopped at this stage (FIG. 4, row 4 and bottom row in left-hand column). In addition, individuals with 3 cotyledons appeared in 8 to 15% of the KK mutant strains. This suggests that the KK strain has some defect in development.

Sections of the wild type and the KK strain hypocotyls prepared on day 5 following the imbibition treatment were stained with Toluidine Blue and examined, whereupon epidermal cells in the KK strain were found to be small and irregularly divided. A similar tendency was observed also in root cross-sections.

By contrast, in most KK strains that were allowed to germinate in a sucrose-free medium, on about day 5 following the imbibition treatment, although a green cotyledon had opened up in the same way as in the wild type, the root showed substantially no growth. Moreover, in most KK strains, growth had stopped at this stage. Thickening of the hypocotyl was not observed. KK strains that germinated in soil took on a form similar to those which germinated in a sucrose-free medium. It was learned from the above that the KK strain seedling phenotype in which the hypocotyl thickens is strongly dependent on the external supply of sucrose. That is, HSI2 and HSI2-L1 (HSL1) were found to have the role of suppressing hypocotyl thickening that arises under sugar induction.

Example 3

Microarray Analysis

A microarray analysis on the wild-type strain and the KK strain was carried out in order to investigate genes in which the expression level is affected by a double deficiency for ΔHSI2 (hsi2-2) and ΔHSI2-L1 (hsl1-1). The total RNA was extracted from KK mutant seedlings (on day 4 after imbibition treatment) in which hypocotyl thickening did not arise. The same procedure was followed as described above in "6. Microarray Analysis" under "Materials and Methods." In two arrays (Agilent Arabidopsis3 oligo Microarray) in which a probe for the 37685 gene of A. thaliana had been fixed, 856 genes were present for which the level of expression in the KK strain was at least twice that in the wild type strain, and 40 genes were present for which the level of expression was at least 30 times higher than in the wild type. Genes for which the level of expression in the KK strain decreased were also present. FIG. 5 shows the group of genes for which the level of expression in the KK strain increased 30-fold, and FIG. 6 shows the group of genes for which the expression level decreased to $\frac{1}{5}^{th}$ or less.

In FIG. 5, genes relating to oil storage proteins are underlined, genes relating to seed storage proteins are italicized, and the transcription factors are marked by asterisks. As is apparent from FIG. 5, in the KK strain, storage protein related genes and the group of genes for which the level of expression increases in late embryogenesis showed a marked increase in the level of expression. That is, in addition to five oleosins which exhibit seed-specific expression and four 2S albumins (at2S1, at2S2, at2S4, at2S5) which are seed storage proteins, the level of expression of the LEC1-like and bZIP67 (DPBF2) transcription factors which are important transcription factors in embryogenesis and which positively regulate seed storage proteins also rose markedly. Furthermore, the level of expression of the transcription regulator factors FUS3, ABI3, bZIP12 and WRI1, which are keys to the development program for middle to late embryogenesis, increased from about 5-fold to about 8-fold.

Also, as shown in FIG. 6, although genes for which the level of expression falls to $\frac{1}{30}^{th}$ the expression level in the wild-type strain were not present in the KK strain, genes relating to photosynthesis were included in the gene group for which the expression level had markedly decreased (underlined in FIG. 6).

From these results, it was apparent that the KK strain manifests a late embryogenesis gene expression pattern even in seedlings, and that the progression of photomorphogenesis is decreased. Hence, HSI2 and HSI2-L1 (HSL1) repressors were found to be essential to suppress the operation of the embryogenesis program in young sprouted plants.

Example 4

Expression Analysis by Quantitative RT-PCR

The manner in which the expression of the group of transcription factors which play an important role in the seed ripening/embryogenesis period in KK strain seedlings changes subsequent to day 4 following the imbibition treatment was investigated. That is, the total RNA was extracted from wild-type strain and KK strain seedlings on days 4, 5, 7 and 9 following the imbibition treatment, and the same procedure was followed as described above in "7. Expression Analysis by Quantitative Real-Time PCR" under "Materials and Methods." FIG. 7A shows the results in a 1% sucrose-containing medium. In addition, the RNA was isolated from 5-day old seedlings grown in media having different sucrose concentrations, and was analyzed to quantitative RT-PCR. The results are shown in FIG. 7B.

As shown in FIG. 7A, in wild-type seedlings in a 1% sucrose-containing medium, the mRNA of both HSI2 and HSI2-L1 (HSL1) is expressed, and the mRNA level of the gene LHCB2:4 used in photosynthesis increased abruptly in the period from day 5 to day 7 when the cotyledon turns green. On the other hand, in the KK strain, compared with the wild-type strain, the expression levels for HSI2 and HSI2-L1 (HSL1) were markedly reduced in both RNA samples, but the genes OleosinS3, At2S3, LEC1, LEC2, FUS3 and WRI1 which are specific to the embryogenesis to seed maturation stages were expressed. In the KK strain, the seed maturation genes were expressed in a different pattern. In 4-day-old KK-strain seedlings, the mRNAs of Ole3 and At2S3 were already more than 30-fold the levels in the wild-type strain, and these mRNA levels increased further up until day 7. Also, dramatic increases in the mRNA levels of the genes LEC1, LEC2 and FUS3 were observed in 4 to 5-day-old seedlings. The expression timing of the master regulator factors for germination resembled the callus-like structure growth initiation period in the hypocotyl. Because the abnormal expression of LEC1 and LEC triggers the embryogenesis program, the activation of these regulator genes brings about the expression of seed maturation genes. As for the mRNA of the WRI1/ASML1 gene, at least 4 days after imbibition treatment, the level of mRNA was already high in the KK strain. Unlike the other genes investigated here, in the wild-type strain, WRI1/ASML1 was expressed in vegetative tissue at a markedly lower level than in the silique. HSI2 and HSI2-L1 (HSL1) appeared to play a more direct role than other genes in regulating the expression of WRI1.

Also, as shown in FIG. 7B, the presence of from 30 mM (1.0%, w/v) to 90 mM (3.1%, w/v) sucrose promotes close to twice as much HSI2 and HSL1 expression as when sucrose is absent, yet 10 mM sucrose was sufficient to suppress the expression of LHCB2;4. KK-strain seedlings grown on a 1% sucrose-containing medium showed a marked decrease in LHCB2;4 expression compared with the wild-type strain. The expression of seed maturation genes in KK-strain seedlings showed a responsiveness that varied with the sucrose concentration. The expression of OleS3, LEC1 and FUS3 was sufficiently induced by 10 mM sucrose, whereas At2S3 and LEC2 exhibited sucrose concentration-dependent increases in expression up to a sucrose concentration of 90 mM. The level of WRI1/ASML1 expression was greatest at a sucrose concentration of 30 mM. These results show that the influence of sucrose in seed maturation gene expression is not uniform, which suggests the possibility that sucrose participates directly or indirectly in the expression of these genes via a plurality of sugar signaling pathways.

Example 5

Accumulation of Seed Storage Products in KK Strain

Using microarray analysis, in the KK strain, a late embryogenesis gene expression profile was observed even in seedlings (Example 3). SDS-PAGE analysis was thus carried out to determine whether seed storage proteins had accumulated in the KK-strain seedlings. The protein was extracted from wild-type and KK-strain seedlings on days 4, 7 and 9 following the imbibition treatment in a sucrose-free medium or a medium containing 1% sucrose, and the same procedure was followed as described above in "8. SDS-PAGE and Western Blotting" under "Materials and Methods." Also, to determine whether a lipid which is a seed-specific storage product has accumulated in the wild-type and KK-strain seedlings, the same procedure was followed as described above in "9. FAT RED 7B Staining" under "Materials and Methods." In addition, to determine whether this staining is due to triacylglycerol (TAG), the same procedure was followed as described above in "10. Lipid Analysis" under "Materials and Methods." Protein samples extracted from dry seeds of the wild-type strain were used as the control in SDS-PAGE, etc. Those results are shown in FIGS. 8A to 8C.

FIG. 8A shows the results of Western blotting following SDS-PAGE. In SDS-PAGE, large disparities between the wild-type strain and the KK strain were not found in the protein extract samples at any stage. Therefore, as shown in FIG. 8A, through Western blotting using an antibody for oleosin S4, which is a seed-specific protein, and using an antibody for 12S globulin, which likewise is a seed-specific protein, the presence or absence of differences in protein expression therebetween was detected. That is, these protein signals were not detected at any stage in wild-type seedlings grown in a sucrose-free medium, whereas oleosin S4 signals were detected in KK strain seedlings on day 4 following the imbibition treatment. Moreover, even in the KK strain, 12S globulin signals were not detected. When seedlings were grown in a sucrose-containing medium, in wild-type seedlings, on day 4 following the imbibition treatment, only oleosin S4 was detected; none of the other proteins was detected. By contrast, in KK strain seedlings, both proteins were detected at all growth stages. These results indicate that, in the KK strain, seed storage proteins accumulate in seedlings in a sucrose-dependent manner.

FIG. 8B shows the results of staining with FAT RED 7B. As shown in FIG. 8B, on day 5 following the imbibition treatment, in wild-type seedlings, only the roots stained faintly, whereas in the KK strain, strong staining occurred in the hypocotyls. On day 12 following the imbibition treatment, substantially no staining occurred in the wild-type strain, whereas in the KK strain, along with the strong staining already observed in the hypocotyl, staining also occurred in the cotyledon. These results suggest that seed storage lipids accumulate in the KK-strain seedlings.

FIG. 8C shows the results of lipid analysis. In wild-type seedlings grown in a sucrose-free medium, only a very small amount of TAG was detected. By contrast, in KK-strain day 4 seedlings, a large amount of TAG accumulation was detected. However, even in the KK strain, on day 9, the TAG had disappeared. These results agreed with the oleosin S4 accumulation pattern shown in FIG. 8A. In wild-type seedlings grown in a sucrose-containing medium, on day 4 following the imbibition treatment, the same level of TAG as in the KK strain had accumulated. However, on day 9, most of the TAG had disappeared. By contrast, in the KK strain, even on day 9, the same level of TAG as on day 4 had accumulated. From the above, seed storage lipid accumulation was found to be sucrose-induced in KK strain seedlings.

Example 6

Embryogenic Callus Formation

In the KK strain, given that the cellular state in late embryogenesis appears also in the seedling and the hypocotyl becomes callus-like, it was thought that the ability for shoot redifferentiation is achieved by means of the plant hormones cytokinin and auxin which regulate plant growth. Therefore, wild-type and KK strain seed were sown in a shoot inducing medium (SIM) containing 0.86 μM of indoleacetic acid and 2.5 μM of $N^6$-($Δ^2$-isopentenyl)-adenine, and the plants were observed. The results are shown in FIG. 9.

Figure 9:
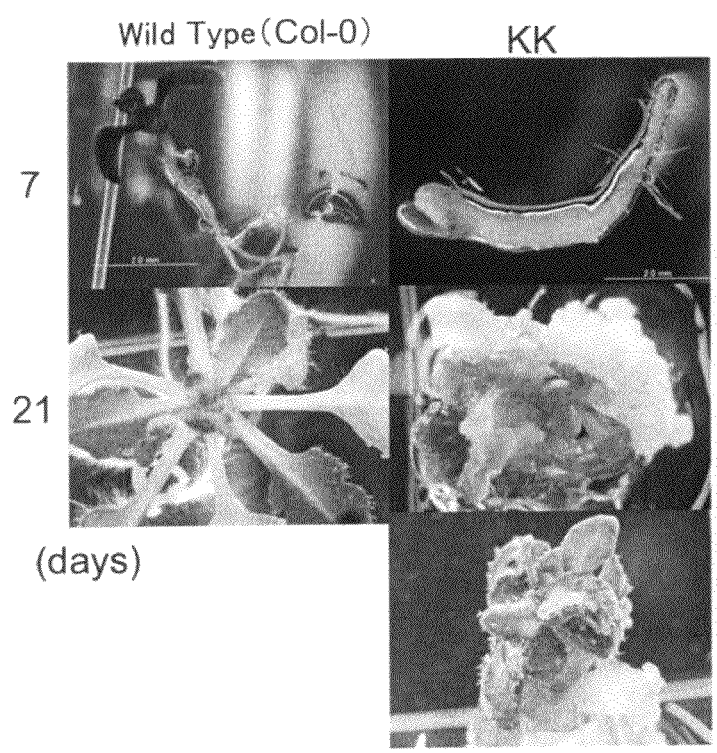
FIG. 9 shows the results (photographs) obtained by collecting hypocotyls from wild-type and KK strains, culturing the hypocotyls in a SIM medium, and examining the cultured hypocotyls. The photographs in the left-hand column are of the wild-type strain, and the photographs in the right-hand column are of the KK strain. The numbers on the left side of the photographs in the left-hand column indicate the number of days elapsed following the imbibition treatment.

As shown in FIG. 9, on day 21 after sowing, the wild-type strain exhibited a state which was largely the same as when grown in a hormone-free medium, whereas the KK strain exhibited organ regeneration such as a redifferentiated shoot and leaves from a callus-like hypocotyl. In the wild-type strain, such shoot regeneration is observed only in calluses that have been pretreated on a callus-inducing medium (CIM).

Next, to verify whether such KK strain calluses are dedifferentiated calluses or embryogenic calluses, the hypocotyls of wild-type seedlings and KK strain seedlings on day 7 following the imbibition treatment were cut off, transplanted to a hormone-free medium, and cultured for 14 days. A total of 48 hypocotyls from KK strain seedlings were cultured. The results are shown in FIG. 10.

Figure 10:
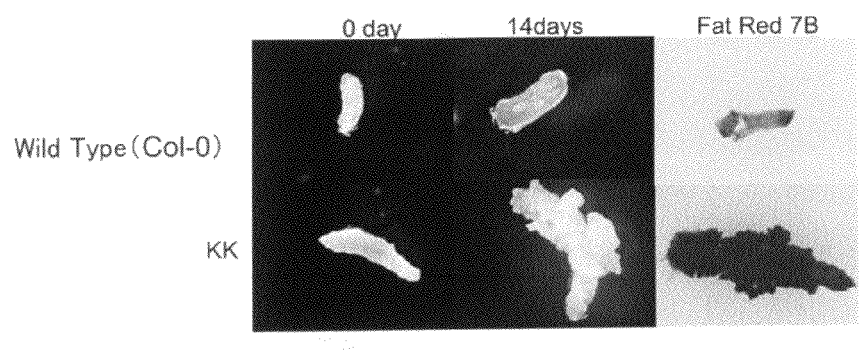
FIG. 10 shows the results (photographs) obtained by cutting off the hypocotyls of wild-type and KK-strain seedlings on day 7 following the imbibition treatment, transferring the hypocotyls to a hormone-free medium, and culturing them for 14 days.

As shown in FIG. 10, callus development did not occur in hypocotyls from wild-type seedlings, whereas 48 hypocotyls from KK strain seedlings exhibited abnormal cell division similar to callus development. Moreover, the hypocotyls of wild-type seedlings were substantially not stained by FAT RED 7B, whereas the entire hypocotyls from KK strain seedlings were strongly stained by FAT RED 7B. This suggested that lipid has accumulated in the same way as in late embryogenesis cells. It was apparent from the above that the KK strain, because the expression by mRNA of transcription factors relating to seed storage proteins and embryogenesis continues even in seedlings, has a hypocotyl with a high cell division activity similar to that of cells during embryogenesis.

Protein was extracted from wild-type and KK-strain hypocotyls cut from seedlings on day 7 after imbibition treatment as noted above, and also from wild-type hypocotyls subjected to callus induction on a CIM medium containing 2.3 μM auxin and 0.46 μM kinetin (Koncz et al.) (CIM callus), following which SDS-PAGE and Western blotting using oleosin S4 antibody and 12S globulin antibody were carried out. The results are shown in FIG. 11.

Figure 11:
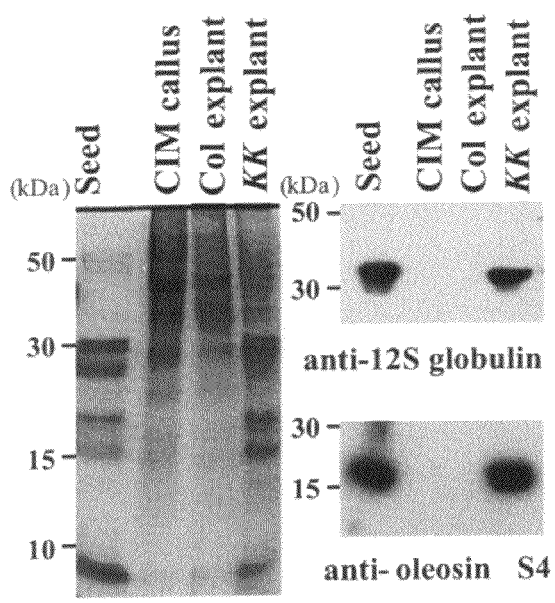
FIG. 11 shows the results of SDS-PAGE analysis and Western blotting analysis using oleosin S4 antibody and 12S globulin antibody on protein extracts from tissue obtained by cutting off the hypocotyls from wild-type and KK-strain seedlings 7 days after water absorption and cultivating the hypocotyls for 14 days in a hormone-free medium, and from CIM calluses of the wild-type strain.

It can be seen from the SDS-PAGE results in FIG. 11 that, as in the seed protein extraction sample used as a control, seed storage protein bands believed to be a 12S globulin A subunit (31 kDa), a 12S globulin B subunit (23 kDa) and a 2S albumin (5 kDa) were detected in the KK strain. Moreover, the KK strain band pattern resembled not only the band pattern for a seed protein extraction sample, but also the band pattern for a wild-type hypocotyl extraction sample. These results appear to indicate that calluses derived from KK strain hypocotyls have the characteristics of both seeds and vegetative tissue. From the Western blotting results also shown in FIG. 11, strong signals for oleosin S4 and 12S globulin were observed in protein extraction samples from seeds serving as the control and from hypocotyl calluses derived from the KK strain. These findings appear to indicate that KK strain hypocotyls form embryogenic calluses independent of plant hormones.

Example 7

Lipid Analysis

Lipids were extracted with 1 mL of a chloroform/methanol mixture (2:1, v/v) from 20 mg of tissue obtained from, respectively, seedlings (wild-type (Col-0 strain) and KK mutant strain) on day 7 following vernalization and from dry seeds (wild-type strain), following which the lipid extracts were centrifuged at 15,000 rpm for 5 minutes. The supernatant was evaporated to dryness, then re-dissolved by the addition of 250 μL of methanol and 15 μL of 2% C15=OMe. Next, 900 μL of methanol and 1 mL of 10% HCl (in methanol) were added to 100 μL of the re-dissolved sample, and methanolysis was carried out at 80° C. for 1 hour. Following methanolysis, 1.5 mL of n-hexane was added and stirring was carried out, then the n-hexane phase was recovered and evaporated to dryness under $N_2$ conditions. The hard-dried sample was re-dissolved in 500 μl, of n-hexane, and the fatty acid content of the fatty acid methyl esters was quantitatively determined by gas chromatography using a GC2010 (Shimadzu Corporation). The results are shown in FIG. 12.

Figure 12:
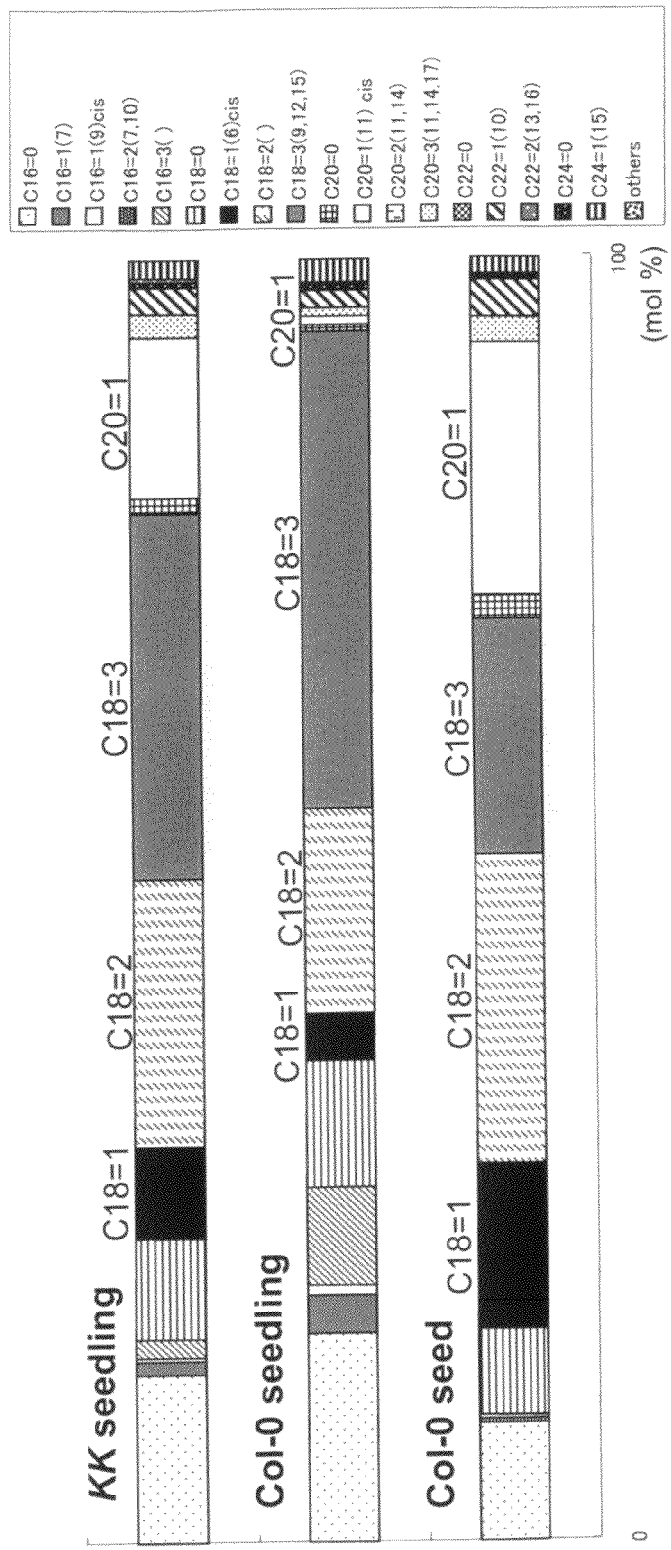
FIG. 12 is a graph showing the fatty acid composition of lipids extracted from KK strain and wild-type seedlings and from dry seeds of the wild-type strain. In the graph, "KK seedling" represents KK strain seedlings, "Col-0 seedling" represents wild-type seedlings, "Col-0 seed" represents wild-type dry seeds. The numbers appended to C indicate the number of carbons and the number of double bonds on the fatty acid.

As shown in FIG. 12, the fatty acid composition extracted from the KK mutant strain seedlings differed from that extracted from the Col-0 wild-type strain, and contained a large amount of seed-specific fatty acids (C18=1, C20=1). It appears from these results that KK seedlings store seed oils.

INDUSTRIAL APPLICABILITY

The present invention may be employed for creating transformed plant bodies. Use is particularly effective for creating transformed plant bodies which control the accumulation of useful storage products such as carbohydrates and lipids.

The invention claimed is:

1. A plant body configured to suppress a function of a sugar-inducible sweet potato sporamin minimal promoter by repressing expression of at least a first protein and a second protein, wherein:
   the first protein comprises a sequence having at least 95% homology to the sequence set forth in SEQ ID NO: 2, or is encoded by a sequence having at least 95% homology to the sequence set forth in SEQ ID NO: 1;
   the second protein comprises a sequence having at least 95% homology to the sequence set forth in SEQ ID NO: 4, or is encoded by a sequence having at least 95% homology to the sequence set forth in SEQ ID NO: 3; and
   the plant body accumulates a storage product at a site other than a normal storage organ by sugar induction.

2. The plant body of claim 1, further comprising an extrinsic factor that represses the expression of genes respectively coding for the first protein and the second protein.

3. The plant body of claim 1, which exhibits sugar-induced late embryogenesis-type gene expression.

4. The plant body of claim 1, which exhibits gene expression in which the expression level increases for one or two or more genes selected from among genes coding for sugar-induced storage product-related proteins and transcription factor genes that positively regulate the genes coding for storage product-related proteins, and in which the expression level decreases for one or two or more genes selected from among photosynthesis-related genes.

5. The plant body of claim 1, wherein the storage product is a storage product in seed.

6. The plant body of claim 1, wherein the storage product contains oil.

7. The plant body of claim 1, wherein the plant body is a seedling that accumulates the storage product in a hypocotyl.

8. The plant body of claim 1, wherein the plant body is a seed.

9. The plant body of claim 8, wherein the seed accumulates a storage product by sugar induction in a hypocotyl of a seedling that is germinated.

10. The plant body of claim 1, wherein the plant body is a cultured tissue.

11. The plant body of claim 10, wherein the cultured tissue is a callus.

12. The plant body of claim 1, wherein the plant body is a plant cell.

13. The plant body of claim 1, wherein the plant body is mouse-ear cress (*Arabidopsis thaliana*) or derived from said plant species.

14. A plant body production method comprising a step of manufacturing a plant body configured to suppress a function of a sugar-inducible sweet potato sporamin minimal promoter by repressing expression of at least a first protein and a second protein, wherein:
   the first protein comprises a sequence having at least 95% homology to the sequence set forth in SEQ ID NO: 2, or is encoded by a sequence having at least 95% homology to the sequence set forth in SEQ ID NO: 1;
   the second protein comprises a sequence having at least 95% homology to the sequence set forth in SEQ ID NO: 4, or is encoded by a sequence having at least 95% homology to the sequence set forth in SEQ ID NO: 3; and
   the plant body accumulates a storage product at a site other than a normal storage organ by sugar induction.

15. A method of producing a plant storage product, the method comprising a step of producing, in the presence of sugar, a storage product in the plant body of claim 1.

16. A plant storage product production enhancer comprising one or two or more nucleic acid construct, wherein the enhancer suppresses expression of at least a first protein and a second protein, wherein:

the first protein comprises a sequence having at least 95% homology to the sequence set forth in SEQ ID NO: 2, or is encoded by a sequence having at least 95% homology to the sequence set forth in SEQ ID NO: 1;

the second protein comprises a sequence having at least 95% homology to the sequence set forth in SEQ ID NO: 4, or is encoded by a sequence having at least 95% homology to the sequence set forth in SEQ ID NO: 3.

17. The plant body of claim 1, wherein the plant body is a seedling.

18. The plant body of claim 1, wherein:
the first protein comprises the sequence set forth in SEQ ID NO: 2, or is encoded by the sequence set forth in SEQ ID NO: 1; and
the second protein comprises the sequence set forth in SEQ ID NO: 4, or is encoded by the sequence set forth in SEQ ID NO: 3.

19. The method of claim 14, wherein:
the first protein comprises the sequence set forth in SEQ ID NO: 2, or is encoded by the sequence set forth in SEQ ID NO: 1; and
the second protein comprises the sequence set forth in SEQ ID NO: 4, or is encoded by the sequence set forth in SEQ ID NO: 3.

20. The plant storage product production enhancer of claim 16, wherein:
the first protein comprises the sequence set forth in SEQ ID NO: 2, or is encoded by the sequence set forth in SEQ ID NO: 1; and
the second protein comprises the sequence set forth in SEQ ID NO: 4, or is encoded by the sequence set forth in SEQ ID NO: 3.

* * * * *